US012736545B2

(12) United States Patent
Rodríguez Martín et al.

(10) Patent No.: US 12,736,545 B2
(45) Date of Patent: Sep. 15, 2026

(54) METHODS FOR APOLIPOPROTEIN DETECTION

(71) Applicants: BIOCROSS, S.L., Boecillo-Valladolid (ES); INSTITUTO DE SALUD CARLOS III, Madrid (ES); CENTRO DE INVESTIGACIÓN BIOMÉDICA EN RED DE ENFERMEDADES NEURODEGENERATIVAS, Madrid (ES)

(72) Inventors: Andrés Rodríguez Martín, Móstoles (ES); Miguel Calero Lara, Valdemorillo (ES); Olga Calero Rueda, Alcorcón (ES); Luis García Albert, Colmenarejo (ES)

(73) Assignees: BIOCROSS, S.L., Boecillo-Valladolid (ES); INSTITUTO DE SALUD CARLOS III, Madrid (ES); CENTRO DE INVESTIGACIÓN BIOMÉDICA EN RED DE ENFERMEDADES NEURODEGENERATIVAS, Madrid (ES)

( * ) Notice: Subject to any disclaimer, the term of this patent is extended or adjusted under 35 U.S.C. 154(b) by 550 days.

(21) Appl. No.: 15/772,515

(22) PCT Filed: Nov. 2, 2016

(86) PCT No.: PCT/EP2016/076457
§ 371 (c)(1),
(2) Date: Sep. 7, 2018

(87) PCT Pub. No.: WO2017/076919
PCT Pub. Date: May 11, 2017

(65) Prior Publication Data

US 2018/0313854 A1 Nov. 1, 2018

(30) Foreign Application Priority Data

Nov. 2, 2015 (EP) .................................... 15382537

(51) Int. Cl.
*G01N 33/68* (2006.01)
*G01N 33/543* (2006.01)
*G01N 33/92* (2006.01)

(52) U.S. Cl.
CPC ... *G01N 33/6896* (2013.01); *G01N 33/54393* (2013.01); *G01N 33/6842* (2013.01); *G01N 33/6893* (2013.01); *G01N 33/92* (2013.01); *G01N 2333/775* (2013.01); *G01N 2800/28* (2013.01); *G01N 2800/2814* (2013.01); *G01N 2800/2821* (2013.01); *G01N 2800/2828* (2013.01); *G01N 2800/2835* (2013.01); *G01N 2800/32* (2013.01); *G01N 2800/50* (2013.01)

(58) Field of Classification Search
CPC ......... G01N 33/6896; G01N 33/54393; G01N 33/6842; G01N 33/6893; G01N 33/92; G01N 2333/775; G01N 2800/28; G01N 2800/2814; G01N 2800/2821; G01N 2800/2828; G01N 2800/2835; G01N 2800/32; G01N 2800/50; G01N 33/49; G01N 33/68
See application file for complete search history.

(56) References Cited

U.S. PATENT DOCUMENTS 4,772,549 A 9/1988 Frossard
5,208,143 A * 5/1993 Henderson ....... G01N 33/54393 435/18
5,945,289 A 8/1999 Lehrer
6,040,182 A * 3/2000 Septak ............ G01N 33/54393 435/29
2005/0255498 A1 11/2005 Aerssens et al.

FOREIGN PATENT DOCUMENTS

JP H10-197528 A 7/1998
WO 00/55635 A1 9/2000
WO 03/031971 A1 4/2003
WO 03/070169 A2 8/2003
WO 2009/108073 A1 9/2009
WO WO-2011109246 A1 * 9/2011 ............. C07K 16/18
WO 2012/006329 A2 1/2012
WO 2013/170057 A2 11/2013

OTHER PUBLICATIONS

VWR 96-well Nunc-immuno product sheet, downloaded on Oct. 9, 2019 from <https://us.vwr.com/store/product/12610575/96-well-nunc-immunotm-plates>.*
Sadowski et al (Am J Pathol 165: 937-948, 2004).*
Thermo Fisher Scientific, 1-3, 2011.*
Florvall et al (J Geront Biol Sc 61A: 1262-1266, 2006).*
Esser Thermo Fisher Scientific 1-7, 2014.*
Uchida et al (J Clin Lab Anal 14: 260-264, 2000).*
Guojun (Mol Neurodeg 7: L10, 2012).*
Schepens et al (Immunotherapy (Editorial) 7: 203-206, Mar. 2015).*
Hydrophobic, Lipid-Binding Plates | Thermo Fisher Scientific—US downloaded on Aug. 8, 2022, one page.*
Wilson et al, (Science 252, 1817-1822, 1991).*
Trougakos et al (Int J Biochem Cell Biol 34: 1430-1448, 2002).*
Machida et al., Clinica Chimia Acta 442:130-135, Mar. 2015.*
Lin et al., Drug Design, Development and Therapy, 9: 5421-5431, Sep. 29, 2015.*
Uchida et al., Journal of Clinical Laboratory Analysis 14:260-264 (Year: 2000).*

(Continued)

*Primary Examiner* — Stacey N Macfarlane
(74) *Attorney, Agent, or Firm* — Seed Intellectual Property Law Group LLP

(57) ABSTRACT

The present invention relates to methods for the detection and quantification of apolipoproteins and isoforms thereof in a sample, as well as to predictive methods of the probability of neurodegenerative or cardiovascular disease development based on apolipoprotein levels as determined by the detection methods of the invention.

16 Claims, 9 Drawing Sheets

(56) References Cited

OTHER PUBLICATIONS

Cukalevski et al, Langmuir, Langmuir 27:14360-14369 (Year: 2011).*
Thermo Scientific, T112—Technical Bulletin "Influence of Buffer on Choice of Protein Quantification Method", published Jan. 2011.*
Lüch et al., Electrophoresis, 18: 2961-2967, (Year: 1997).*
Carey et al., Clinical Biochemistry, 49: 1406-1411 (Year: 2016).*
Lee et al., "Apolipoprotein E Promotes β-Amyloid Trafficking and Degradation by Modulating Microglial Cholesterol Levels," *The Journal of Biological Chemistry* 287(3):2032-2044, 2012.
Polis et al., "Isolation of a Crystalline Albumin from Milk," *J. Biol. Chem.* 187:349-354, 1950 (7 pages).
Tokuda et al., "Lipidation of apolipoprotein E influences its isoform-specific interaction with Alzheimer's amyloid β peptides," *Biochem. J.* 348:359-365, 2000.
Wright et al., "Quantitation of Apolipoprotein E in Rabbit Sera with a Competitive Enzyme-Linked Immunosorbent Assay," *Journal of Immunological Methods* 58:143-153, 1983.
Pool et al., "The Development of an Elisa for Chicken Apolipoprotein II Quantitation" *Journal of Immunoassay & Immunochemistry* 23(4):439-449, 2002.
Raffaï et al., "Binding of an Antibody Mimetic of the Human Low Density Lipoprotein Receptor to Apolipoprotein E Is Governed through Electrostatic Forces," *Journal of Biological Chemistry* 275(10):7109-7116, 2000.
Simon et al., "Total ApoE and ApoE4 Isoform Assays in an Alzheimer's Disease Case-control Study by Targeted Mass Spectrometry (n=669): A Pilot Assay for Methionine-containing Proteotypic Peptides," *Molecular & Cellular Proteomics* 11(11):1389-1403, 2012.
Uchida et al., "Sandwich ELISA for the Measurement of Apo-E4 Levels in Serum and the Estimation of the Allelic Status of Apo-E4 Isoforms" *Journal of Clinical Laboratory Analysis* 14:260-264, 2000.
Hesse et. al., "Measurement of Apolipoprotein E (apoE) in Cerebrospinal Fluid," *Neurochemical Research* 25(4): 511-517, 2000.
Høgåsen et al., "Quantitation of vitronectin and clusterin. Pitfalls and solutions in enzyme immunoassays for adhesive proteins," *Journal of Immunological Methods* 160(1):107-115, 1993.

* cited by examiner

METHODS FOR APOLIPOPROTEIN DETECTION

TECHNICAL FIELD

The present invention relates to methods for the detection and quantification of apolipoproteins and isoforms thereof in a sample, as well as to predictive methods to estimate the probability of neurodegenerative or cardiovascular disease development based on apolipoprotein levels as determined by the detection methods of the invention.

BACKGROUND ART

Apolipoprotein E (apoE) is a 34 kDa glycoprotein involved in lipid metabolism. The human APOE gene coding for this protein is polymorphic and is located on chromosome 19. There are three common codominant alleles (ε2, ε3 and ε4) that encode three apoE protein isoforms: E2, E3 and E4. These isoforms differ at the amino acid residues 112 and 158. Isoform E2 has cysteine residues at both sites, E4 has arginine residues at both sites, while E3, the most common form, has a cysteine at position 112 and an arginine at position 158. These differences have profound effects on the biological functions of apoE. The lipid-binding activity of these isoforms is different: E2 and E3 bind preferentially to high-density lipoproteins (HDL), whereas E4 prefers very low-density lipoproteins (VLDL). These biochemical differences may be responsible for the association of the isoforms with different pathological processes. The isoform E4 is associated with higher levels of cholesterol and increased risk for coronary heart and Alzheimer's diseases. In contrast, isoform E2 shows a protective effect against Alzheimer's disease, but it is associated with familial type III hyperlipoproteinemia. Thus, interest in APOE genotypes or apoE isoforms is high for epidemiological research, patient stratification and identification of those at increased risk of for clinical trials and prevention.

Several methods are commonly used for genotyping the three major APOE haplotypes. The more frequently used methods are: PCR-RFLP (Polymerase Chain Reaction-Restriction Fragment Length Polymorphism), capillary electrophoresis, PCR plus sequencing or mass spectrometry, ARMS-PCR (Amplification Refractory Mutation System-PCR) and SSP-PCR (Simple Sequence Specific Primer-PCR), Real Time PCR detection by fluorescence melting curves, FRET (Fluorescent Resonance Energy Transfer), allele specific RT-PCR and TaqMan® probes. However, all of these APOE gene-based methods require an informed consent for DNA extraction and analysis of genetic information, and cannot easily implemented in the clinical analysis routine.

Mainly for research purposes, several alternative biochemical (non-genetic) methods are in use for the sensitive characterization of apoE isoforms. The most commonly used are isoelectric focusing (IEF) and sandwich ELISA, which rely in the characterization of apoE from biological fluids such as plasma or CSF. For analytical IEF of apoE, isoelectrofocusing of proteins in immobilized pH gradients is followed by immunodetection of the separated isoforms by using an anti-apoE antibody. The specific apoE-bands pattern allows the detection of the different apoE isoforms present in the sample. This technique has the advantage that could detect rare apoE variants, other than the apoE E2, E3 and E4 isoforms; however, it is technically demanding and time consuming.

ELISA (enzyme-linked immunosorbent assay) techniques use antibodies in order to capture the target protein. Sandwich ELISA may be used to check for the presence of the apoE E4 isoform, and rely in the use of two antibodies (capture and reporter antibodies), of which one of them has to be specific for the E4 isoform. There are several commercially available ELISA kits for the detection of apoE E4 (e.g. ApoE4/pan-ApoE ELISA Kit, MBL #7635); however, probably due to inherent technical limitations, this methodology has not been implemented in clinical routine settings.

Methods to predict disease development based on apolipoprotein levels have been described in the art. U.S. Pat. No. 5,945,289A relates to methods for assessing the predisposition of a subject to develop cancer prostate based on the genotyping of ApoE alleles by means of PCR.

However, there is still a need in the state of the art to develop reliable and accurate methods for apolipoprotein detection and apolipoprotein isoform determination that allow fast and reliable determination of apolipoproteins in a sample. Said methods would be of interest for predicting the development of some disease related to apolipoprotein, or particular isoforms thereof, presence or absence.

BRIEF SUMMARY OF THE INVENTION

The authors of the present invention have developed a methodology for the detection, quantification and analysis of apolipoproteins and isoforms thereof. This methodology is based on the particular binding properties of apolipoproteins to a surface, particularly a polystyrene surface, which avoid the need of using a capture antibody or of previous isolation procedures for the detection or quantification. The authors have shown that apolipoproteins, particularly apoE, are specifically captured by polystyrene surfaces (including ELISA plates, luminex beads, or turbidimetric beads). A particular apolipoprotein isoform, such as apoE E4, once it is bound to the surface, may be detected by an anti-apoE4 antibody, so detection and quantification of apoE4 isoform in a sample is achieved. This quantitation can be correlated with the presence of the APOE ε4 genotype, either in heterozygosity (ε2/ε4, ε3/ε4) or in homozygosity (ε4/ε4). Taking into account that these binding properties are common to other apolipoproteins, this methodology may be applied as well to other apolipoproteins, including apoAI, apoAIV, apoCI, apoCII, apoCIII, and apoJ (clusterin).

Thus, in a first aspect, the present invention is related to an in vitro method for the detection and/or quantification of an apolipoprotein selected from the group consisting of apoCI, apoAIV, apoCI, apoCII, apoCIII, apoE and apoJ (clusterin) or an isoform thereof in a sample that comprises:

(i) Contacting the sample with a polystyrene or a polycarbonate surface under suitable conditions for the binding of the apolipoprotein or the isoform thereof to the surface, wherein the surface contains no antibodies specific for said apolipoprotein or isoform thereof bound to it, (ii) Contacting the surface to which the apolipoprotein or the isoform thereof is bound formed in step (i) with an antibody specific for said apolipoprotein or for said isoform thereof under suitable conditions for the formation of a complex between the antibody and the apolipoprotein or the isoform thereof, and (iii) Detecting the complexes formed in step (ii)

wherein the polystyrene surface or the polycarbonate surface is not treated before contacting the sample or is blocked with albumin prior to contacting the sample.

In a further aspect, the invention relates to an in vitro method for determining the relative amount of an isoform of a given apolipoprotein selected from the group consisting of apoCI, apoAIV, apoCI, apoCII, apoCIII, apoE and apoJ (clusterin) with respect to the total content of said apolipoprotein in a sample that comprises:

(i) Contacting the sample with a polystyrene or a polycarbonate surface under suitable conditions for the binding of the apolipoprotein to the surface, wherein the surface contains no antibodies specific for said apolipoprotein bound to it, (ii) Contacting the surface to which the apolipoprotein is bound formed in step (i) with a first antibody specific for said apolipoprotein isoform and with a second antibody which is capable of binding to all the isoforms of said apolipoprotein present in the sample, wherein said contacting is carried out under conditions suitable for the formation of a first complex comprising the first antibody and the apolipoprotein isoform and for the formation of a second complex comprising the second antibody and all the isoforms of said apolipoprotein, (iii) Detecting the first and second complexes formed in step (ii) and (iv) Determining the relative amounts of the isoform with respect to the total apolipoprotein content based on the levels of the first and second complex obtained in step (iii)

wherein the polystyrene surface or the polycarbonate surface is not treated before contacting the sample or is blocked with albumin prior to contacting the sample.

In another aspect, the invention relates to a method for determining the allelic dosage of haplotypes associated with the expression of an apolipoprotein isoform of an apolipoprotein selected from the group consisting of apoCI, apoAIV, apoCI, apoCII, apoCIII, apoE and apoJ (clusterin) in a subject comprising, (i) Contacting a protein-containing sample from said subject derived from a tissue wherein the apolipoprotein isoform is expressed with a polystyrene or polycarbonate surface under suitable conditions for the binding of the apolipoprotein isoform to the surface, wherein the surface contains no antibodies specific for said apolipoprotein isoform bound to it, (ii) Contacting the surface to which the apolipoprotein is bound, formed in step (i) with at least one antibody specific for the apolipoprotein isoform under suitable conditions for the formation of a complex between the antibody and the apolipoprotein isoform, (iii) Determining the allelic dosage of the apolipoprotein isoform by correlating the amount of complex formed in step (ii) with the number of alleles encoding said genetic variant wherein the polystyrene surface or the polycarbonate surface is not treated before contacting the sample or is blocked with albumin prior to contacting the sample.

In another aspect, the invention relates to a method for determining the probability that a subject develops a neurodegenerative disease that comprises determining in a sample from said subject the levels of apoE E4 isoform by a method according to any of methods of the invention, wherein if the apoE E4 levels are above a reference value, then it is indicative that the subject has a high probability of suffering from a neurodegenerative disease.

In another aspect, the invention relates to a method for determining the probability that a subject develops a neurodegenerative disease that comprises determining in said subject the allelic dosage of the haplotype encoding the apoE4 isoform by a method according to any of methods of the invention, wherein the presence of one or two apoE4 alleles in the genome of the subject is indicative that the subject has a high probability of suffering from a neurodegenerative disease, and wherein the presence of no apoE4 alleles in the genome of the subject is indicative that the subject has a low probability of suffering from a neurodegenerative disease.

In another aspect, the invention relates to a method for determining the probability that a subject develops a cardiovascular disease that comprises determining in a sample from said subject the levels of an apolipoprotein isoform by a method according to any of methods of the invention, wherein if said apolipoprotein isoform levels are above a reference value, then it is indicative that the subject has a high probability of suffering from a cardiovascular disease.

In yet another aspect, the invention relates to a method for determining the probability that a subject develops a cardiovascular disease that comprises determining in said subject the allelic dosage of the haplotype encoding an apolipoprotein isoform by a method according to any of methods of the invention, wherein the presence of one or two alleles of said apolipoprotein isoform in the genome of the subject is indicative that said subject has a higher probability of suffering from a cardiovascular disease, and wherein the presence of no alleles of said apolipoprotein isoform in the genome of the subject is indicative that said subject has a lower probability of suffering from a cardiovascular disease.

In a another aspect, the invention relates to a kit comprising a polystyrene or a polycarbonate surface and an antibody specific for an apolipoprotein or isoform thereof, wherein the kit does not comprise a second antibody specific for said apolipoprotein or isoform thereof.

In another aspect, the invention relates to the use of a kit as above for detecting and/or quantifying an apolipoprotein selected from the group consisting of apoAI, apoAIV, apoCI, apoCII, apoCIII, apoE and apoJ (clusterin) or an isoform thereof, wherein the polystyrene or polycarbonate surface is blocked with albumin.

DETAILED DESCRIPTION OF THE INVENTION

Figure 1:
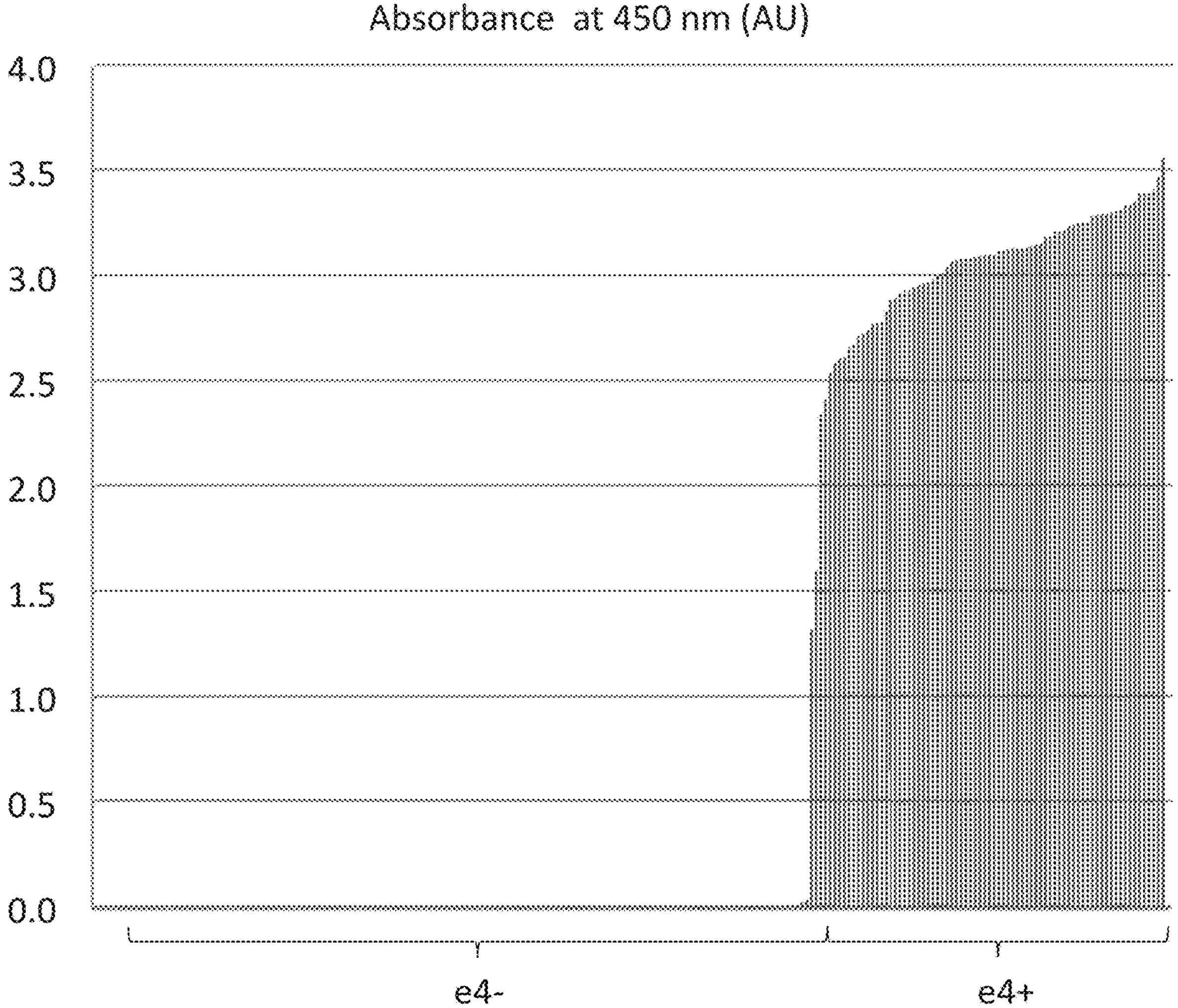
FIG. 1 shows the analysis of the presence of the apoE E4 isoform in 157 plasma samples containing no apoE4 isoform, and 73 samples containing apoE4.

The authors of the present invention have found that apolipoproteins from biological fluids, particularly apolipoprotein apoE and, more in particular, isoform 4 of apoE (apoE E4), have a stable high-affinity binding capacity to polystyrene surfaces. Based on this property, the inventors have developed methods for detecting and quantifying apolipoproteins that do not require isoelectrofocusing or capture antibodies. The invention describes a simple, reliable and cost-effective method that can be easily implemented in research labs as well as in a clinical analysis setting. Since apolipoproteins have been related to cardiovascular and neurovascular risk and to neurodegeneration, the methods provided herein provide valuable information for patient stratification and identification of those at increased risk of Alzheimer disease (AD) and cardiovascular disorders. This methodology can be also exploited for the characterization of other apolipoproteins as protein biomarkers, namely apoCI, apoCII, apoCIII, apoAI and clusterin, and it is relevant to the analysis of easily accessible biological fluids such as blood or urine.

Definitions

The term "allele", as used herein, relates to one of two or more forms of a gene, locus or genetic polymorphism. Sometimes, different alleles can result in different traits; however, other times, different alleles will have the same result in the expression of a gene. Most multicellular organisms have two sets of chromosomes, that is, they are diploid. These chromosomes are referred to as homologous chromosomes. Diploid organisms have one copy of each gene (and one allele) on each chromosome. If both alleles are the same, they are homozygotes. If the alleles are different, they are heterozygotes.

The term "allelic dosage", as used herein, relates to the number of copies of a specific allele variant, ranging from 0 to 2 in a diploid organism.

The term "Alzheimer's disease" or "AD", as used herein, refers a mental deterioration associated with specific degenerative brain disease that is characterized by senile plaques, neuritic tangles and progressive neuronal loss which manifests clinically in progressive memory deficits, confusion, behavioral problems, inability to care for oneself, gradual physical deterioration and, ultimately, death. As used herein, this term is intended to include all the stages of the disease.

The terms "antibody", "immunoglobulin" and the like terms refer to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. An exemplary immunoglobulin (antibody) structural unit is composed of two pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The C-terminal ends of each heavy chain are disulfide bonded together, and form the constant region of the antibody. Depending on the amino acid sequence of the constant domain of their heavy chains, antibodies can be assigned to different "classes". There are five-major classes of antibodies: IgA, IgD, IgE, IgG, and IgM, and several of these may be further divided into "subclasses" (isotypes), e.g., IgG1, IgG2, IgG3, IgG4, IgA, and IgA2. Full-length immunoglobulin "light chains" (of about 25 kDa or about 214 amino acids) comprise a variable region of about 1-10 amino acids at the NH2-terminus and a kappa or lambda constant region at the COOH-terminus. Full-length immunoglobulin "heavy chains" (of about 50 kDa or about 446 amino acids) similarly comprise a variable region (of about 116 amino acids) and one of the aforementioned heavy chain constant regions or classes, e.g., gamma (of about 330 amino acids). The subunit structures and three-dimensional configurations of different classes of immunoglobulins are well known.

The term "apolipoprotein", as used herein, relates to a protein that binds lipids to form a lipoprotein. This protein may function as enzyme cofactor, receptor ligand and lipid transfer carrier that regulates the metabolism of proteins and their uptake in tissues. This term encompasses a number of classes of apolipoproteins as follows apoA (including isoforms apoA-I, apoA-II, apoA-IV and apoA-V), apoB (including isoforms apoB48 and apoB100), apoC (including isoforms apoC-I, apoC-II, apoC-III and apoC-IV), apoD, apoE (including apoE2, apoE3 and apoE4 isoforms), apoH and apoJ (clusterin), as well as apoF, apoG, apoL, apoM, apoN and apoO. In a particular embodiment, the apolipoprotein is apoE.

The term "apolipoprotein A-I" or "Apo A-I", or "ApoAI" as used herein, refers to a protein that is the major protein component of high density lipoproteins (HDL) in plasma. ApoAI is a cofactor for lecithin cholesterolacyltransferase (LCAT) which is responsible for the formation of most plasma cholesteryl esters. In humans, apoAI is encoded by the APOAI gene. The apoA-I can be from any origin, for example human, bovine, murine, equine, canine, etc. In a particular embodiment, the apo A-I is the human protein with the UniProt accession number P026547 (release of May 16, 2014).

The term "apolipoprotein A-IV" or "Apo A-IV", or "ApoAIV" as used herein, refers to a protein obtained after proteolysis of a primary translation product of 306-residue proprotein. The apo A-IV can be from any origin, for example human, bovine, murine, equine, canine, etc. In a particular embodiment, the Apo A-IV is the human protein with the UniProt accession number P06727 (release of May 16, 2014). Human apoA-IV isoforms include apoA-IV-la (T347S) and apoA-IV-2 (Q360H).

The term "apolipoprotein C-I" or "Apo C-I", or "ApoCI", as used herein, refers to a protein normally found in plasma and responsible for the activation of esterified lecithin cholesterol with an important role in the exchange of esterified cholesterol between lipoproteins and in removal of cholesterol from tissues. In humans, apoC-I is encoded by the APOC1 gene. The Apo C-I can be from any origin, for example human, bovine, murine, equine, canine, etc. In a particular embodiment, the apoC-I is the human protein with the UniProt accession number P02654 (release of May 16, 2014). ApoC-I isoforms include acidic (apoC-IA), and basic (apoC-IB), based upon their calculated isoelectric points.

The term "apolipoprotein C-II" or "Apo C-II", or "Apo CII", as used herein, refers to a protein normally found in plasma where it is a component of very low density lipoproteins (VLDL) and chylomicrons. In humans, apoC-II is encoded by the APOC2 gene. The apoC-II can be from any origin, for example human, bovine, murine, equine, canine, etc. In a particular embodiment, the apoC-II is the human protein with the UniProt accession number P02655 (release of May 16, 2014).

The term "apolipoprotein C-III" or "Apo C-III", or "Apo CIII", as used herein, refers to a protein found as a component of very low density lipoproteins (VLDL). ApoCIII is a relatively small protein containing 79 amino acids that can be glycosylated at threonine-74. It inhibits lipoprotein lipase and hepatic lipase. In humans, apo C-III is encoded by the APOC3 gene. The Apo C-III can be from any origin, for example human, bovine, murine, equine, canine, etc. In a particular embodiment, the apo C-III is the human protein with the UniProt accession number P02656 (release of May 16, 2014). ApoC-III is present in three isoforms that are termed apoC-$III_0$, apoC-$III_1$, and apoC-$III_2$, depending on the number of sialic acid molecules (0 to 2) terminating the oligosaccharidic portions of the protein. Each isoform has been shown to contribute, respectively, to approximately 10, 55, and 35% of the total apoC-III levels in circulation.

The term "apolipoprotein-E" or "Apo-E", or "ApoE" as used herein, refers to a protein found in chylomicrons and intermediate-density lipoproteins (IDLs) that is essential for the normal catabolism of triglyceride-rich lipoprotein constituents. In humans, apolipoprotein E is encoded by the gene ApoE, which is a polymorphic gene with three major alleles, ε2, ε3, and ε4, which encodes the isoforms ApoE2 (cys112, cys158), ApoE3 (cys112, arg158), and ApoE4 (arg112, arg158). The apolipoprotein E can be from any origin, for example human, bovine, murine, equine, canine, etc. In a particular embodiment, the Apo E is the human protein with the UniProt accession number P02649 (May 16, 2014).

The term "apolipoprotein E type 2 isoform" or "apo E2", as used herein, refers to the isoform E2 of the protein apolipoprotein E, which is defined by the presence of the residue cysteine in positions 112 and 158 of the amino acid sequence.

The term "apolipoprotein E type 3 isoform" or "apo E3", as used herein, refers to the isoform E3 of the protein apolipoprotein E, which is defined by the presence of the residue cysteine in position 112 and of the residue arginine in position 158 of the amino acid sequence.

The term "apolipoprotein E type 4 isoform" or "apo E cod variable" or "apo E4", as used herein, refers to the isoform E4 of the protein apolipoprotein E, which is defined by the presence of the residue arginine in positions 112 and 158 of the amino acid sequence.

The term "apolipoprotein-J" or "Apo-J", or "ApoJ" or "clusterin", or "complement lysis inhibitor" or "CLI", or "sulfated glycoprotein 2" or "SGP2" or "SP-40,40" or "testosterone-repressed prostate message 2" or "TRPM2", as used herein, refers to a secretory, heterodimeric glycoprotein that influences immune regulation, cell adhesion, transformation, lipid transportation, tissue remodelling, membrane recycling and cell-cell interactions. Clusterin is synthesized as a 449 amino acid polypeptide that is post-translationally cleaved at an internal bond between Arg 227 and Ser 228. The apolipoprotein J can be from any origin, for example human, bovine, murine, equine, canine, etc. In a particular embodiment, the ApoJ is the human protein with the UniProt accession number P10909 (May 16, 2014).

The term "cardiovascular disease" or "cardiovascular disorder", as used herein, relates to diseases affecting the heart or blood vessels or both or associated with the cardiopulmonary and circulatory systems including but not limited to ischemia, angina, edematous conditions, artherosclerosis, coronary heart disease, LDL oxidation, adhesion of monocytes to endothelial cells, foam-cell formation, fatty-streak development, platelet adherence, and aggregation, smooth muscle cell proliferation, reperfusion injury, high blood pressure, thrombotic disease, arrhythmia (atrial or ventricular or both); cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue, endotoxic, surgical, or traumatic shock; hypertension, valvular heart disease, heart failure, abnormal blood pressure; shock; vasoconstriction (including that associated with migraines); vascular abnormality, inflammation, and insufficiency limited to a single organ or tissue.

The term "detergent", as used herein, also known as "surfactant", relates to amphipathic surface-active agents that, when added to a liquid, reduce surface tension of the liquid in comparison to the same liquid in the absence of the detergent. Detergents are also capable of preventing aggregation of proteins and of preventing non-specific interaction or binding of contaminants to a protein of interest. Detergents according to the present invention include, without limitation, non-ionic (neutral), anionic, cationic, or zwitterionic detergents.

Examples of non-ionic or neutral detergents include, without limitation, detergents of the Tween series (polysorbate), such as Tween® 20 (polysorbate 20), Tween® 21 (polysorbate 21), Tween® 40 (polysorbate 40), Tween® 60 (polysorbate 60), Tween® 61 (polysorbate 61), Tween® 65 (polysorbate 65), Tween® 80 (polysorbate 80), Tween® 81 (polysorbate 81), Tween® 85 (polysorbate 85), detergents of the Span® series, such as Span® 20; detergents of the Tergitol series, such as Tergitol Type 15-S-12; detergents of the Brij® series, such as Brij® 35, Brij® 56, Brij® 72, Brij® 76, Brij® 92V, Brij® 97, Brij® 58P; detergents of the Tween series, such as Tween® 20, Tween® 21, Tween® 40, Tween® 60, Tween® 61, Tween® 65, Tween® 80, Tween® 81, Tween® 85; detergents of the Triton® series, such as Triton® X-100, Triton® X-114, Triton® CF-21, Triton® CF-32, Triton® DF-12, Triton® DF-16, Triton® GR-5M, Triton® X-102, Triton® X-15, Triton® X-151, Triton® X-207, Triton® X-165, Triton® X-305, Triton® X-405, Triton® X-45, Triton® X-705-70, or a non-ionic conservative variant of at least one of said detergent.

Examples of anionic detergents include, without limitation, cholic acid and derivatives thereof, taurocholic acid, Triton X-200, Triton W-30, Triton-30, Triton-770, dioctylsulfo succinate, $N_5$N-dimethyldodecylamine N-oxide, sodium 1-alkylsulfonates, N-lauroylsarcosine or fatty acid salts.

Examples of cationic detergents include, without limitation, mono and di-methyl fatty amines, alkyl trimethyl ammonium salts, dialkyl dimethyl ammonium salts, alkyl amine acetates, trialkylammonium acetates, alkyldimethylbenzyl ammonium salts, dialkymethylbenzyl ammonium salts, alkylpyridinium halide and alkyl (alkyl substituted) pyridinium salts, alkylthiomethylpyridinium salts, alkylamidomethylpyridinium salts, alkylquinolinium salts, alkylisoquinolinium salts, N,N-alkylmethylpyrollidonium salts, 1,1-dialkylpiperidinium salts, 4,4-dialkylthiamorpholinium salts, 4,4-dialkylthiamorpholinium-1-oxide salts, methyl his (alkyl ethyl)-2-alkyl imidazolinium methyl sulfate (and other salts), methyl bis(alkylamido ethyl)-2-hydroxyethyl ammonium methyl sulfate (and other salts), alkylamidopropyl-dimethylbenzyl ammonium salts, carboxyalkyl-alkyldimethyl ammonium salts, alkylamine oxides, alkyldimethyl amine oxides, poly(vinylmethylpyridinium) salts, poly(vinylpyridine) salts, polyethyleneimines, trialkylphosphonium bicarbonates (and other salts), trialkylmethylphosphonium salts, alkylethylmethylsulfonium salts, and alkyldimethylsulfoxonium salts.

Examples of zwitterionic detergents include, without limitation, 3-[(3-cholamidopropyl)dimethylammonio]-1-propanesulfonate (CHAPS); 3-[(3-cholamidopropyl)dimethylammonio]-2-hydroxy-1-rhoropanesulfonate (CHAPSO); N-(alkyl C10-C16)-N,N-dimethylglycinebetaine (EMPIGEN BB); Caprylylsulfobetaine (SB3-10); 3-[N,N-dimethyl(3-myristoylaminopropyl)ammonio]propanesulfonate (Amidosulfobetaine-14; ASB-14); N-tetradecyl-N,N-dimethyl-3-ammonio-1-propoanesulfonate(3-14 Detergent; ZWITTERGENT); N-dodecyl-N,N'-dimethyl-3-ammonio-1-propanesulfonate; N-octadecyl-N,N-dimethyl-3-ammonio-1-propanesulfonate; N-decyl-N,N-dimethyl-3-ammonium-1-propanesulfonate; Mirataine CB; Mirataine BB; Mirataine CBR; Mirataine ACS; Miracare 2MHT and Miracare 2MCA.

The expression "determining the probability" or "prediction of the probability", or similar, as used herein, is synonymous of the expression "assessing the probability" or "assessment of the probability", and means that the present invention makes it possible to predict, estimate or evaluate the probability of a patient of developing a disease, particularly a neurodegenerative disease or a cardiovascular disease. The prediction of probability generally implies that the probability is either increased or reduced. As it will be understood by those skilled in the art, the prediction, although preferred to be, need not be correct for 100% of the subjects to be evaluated. The term, however, requires that a statistically significant portion of the patients can be identified as having an increased probability of having a disease, particularly a neurodegenerative disease or a cardiovascular disease. Whether a subject is statistically significant can be determined without further ado by the person skilled in the art by using various well known statistic evaluation tools, e.g., determination of confidence intervals, p-value determination, Student's t-test, Mann-Whitney test, etc. Details can be found in Dowdy and Wearden, Statistics for Research, John Wiley & Sons, New York 1983. Preferred confidence intervals are at least 50%, at least 60%, at least 70%, at least 80%, at least 90% at least 95%. The p-values are, preferably 0.05, 0.025, 0.001, 0.0001 or lower.

The term "haplotype", as used herein, refers to a specific group of genes that a progeny inherits from one parent. Particularly, the haplotype encompasses the collection of particular alleles on a chromosome, which are likely to be inherited together. A haplotype can comprise two or more alleles.

The term "immunoturbidimetry", as used herein, relates to a technique for the detection of an analyte in a sample based on the reaction of the analyte with an antibody, which leads to the formation of an antibody-antigen immune complex between the analyte and the antibody that precipitates, increasing the turbidity of the sample. As a result, when light is passed through the reaction solution, some light is scattered by the sample, some light is absorbed by the sample and the rest passes through the sample. The amount of absorbed light is directly proportional to the analyte concentration or, in other words, the transmittal light signal is directly proportional to the analyte concentration. According to the present invention, the analyte to be detected by immunoturbidimetry is an apolipoprotein or isoform thereof, particularly an apolipoprotein selected from the group consisting of apoAI, apoAIV, apoCI, apoCII, apoCIII, apoE and apoJ (clusterin) and isoforms thereof, more particularly apoE and/or apoE isoforms apoE2, apoE3 and apoE4, more preferably apoE4. In a particular embodiment of the invention, the immunoturbidimetry assay is LEIT (Latex-Enhanced Immunoturbidimetry Technology).

The term "neurodegenerative disease", as it is used herein, is related to diseases which result from the degeneration or deterioration of nervous tissue, particularly of neurons, leading over time to a dysfunction or to a disability; the term degeneration includes loss of cell viability, loss of cell function and/or loss of the number of cells (neurons or others). Illustrative, non-limiting, examples of neurodegenerative diseases include Alzheimer's disease (AD), Huntington's disease, Parkinson's disease, amyotrophic lateral sclerosis (ALS), multiple sclerosis, etc. In a particular embodiment, said neurodegenerative disease is AD.

The term "oxidizing agent", as used herein, relates to a chemical species that removes an electron from another species in a redox (oxidation-reduction) reaction.

The term "polycarbonate", as used herein, relates to a group of thermoplastic polymers containing carbonate groups (—O(C═O)—O) in their chemical structures.

The term "polystyrene", as used herein, relates to a synthetic, aromatic, thermoplastic, polymer made from the monomer styrene. Polystyrene can be solid or foamed.

The term "protease", as used herein, also known as "peptidase", refers to an enzyme catalyzing the hydrolysis of peptide bonds in proteins. Illustrative, non-limiting examples of proteases include serine peptidases, threonine peptidases, cysteine peptidases, aspartyl peptidases, metallopeptidases and glutamyl peptidases. In a particular embodiment, the protease is pepsin, trypsin or chymotrypsin. As used in the present description, the term "pepsin" refers to a protease catalyzing the hydrolysis of peptide bonds between hydrophobic amino acids and preferably aromatic amino acids, such as phenylalanine, tryptophan and tyrosine.

The term "reducing agent", as used herein, relates to a compound that loses an electron to another chemical species (the oxidizing agent) in a redox (oxidation-reduction) chemical reaction. The loss of electrons by the reducing agent results in its oxidation.

The term "reference value", as used herein, relates to a predetermined criteria used as a reference for evaluating the values or data obtained from the samples collected from a subject. The reference value or reference level can be an absolute value; a relative value; a value that has an upper or a lower limit; a range of values; an average value; a median value; a mean value; or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested.

The term "salt", as used herein, relates to any form of a compound in ionic form, or charged and coupled to a counter-ion (a cation or anion), or in solution. The definition includes in particular pharmaceutically acceptable salts.

The term "sample", as used herein refers to biological material isolated from a subject and therefore includes biological samples. Said sample can contain any biological material suitable for detecting the desired marker and can comprise cells and/or non-cellular material from the subject. In general, a sample can be isolated from any suitable biological tissue or fluid. Particular preferred samples according to the invention include, without limitation, of blood, plasma, serum, saliva, urine and cerebrospinal fluid (CSF). In an embodiment of the invention, the sample is a plasma sample.

The term "subject", or "individual" or "animal" or "patient" includes any subject, particularly a mammalian subject, for whom therapy is desired. Mammalian subjects include humans, domestic animals, farm animals, and zoo or pet animals such as dogs, cats, guinea pigs, rabbits, rats, mice, horses, cattle, cows, and so on. In a particular embodiment, the subject is a human.

Apolipoprotein Detection and Quantification Method of the Invention

In a first aspect, the invention relates to an in vitro method for the detection and/or quantification of an apolipoprotein or an isoform thereof in a sample (first method of the invention) that comprises:

(i) Contacting the sample with a polystyrene or a polycarbonate surface under suitable conditions for the binding of the apolipoprotein or the isoform thereof to the surface, wherein the surface contains no antibodies specific for said apolipoprotein or isoform thereof bound to it, (ii) Contacting the surface to which the apolipoprotein of the isoform thereof is bound formed in step (i) with an antibody specific for said apolipoprotein or for said isoform thereof under suitable conditions for the formation of a complex between the antibody and the apolipoprotein or the isoform thereof, and (iii) Detecting the complexes formed in step (ii).

In a particular embodiment, the invention relates to an in vitro method for the detection and/or quantification of an apolipoprotein selected from the group consisting of apoAI, apoAIV, apoCI, apoCII, apoCIII, apoE and apoJ (clusterin) or an isoform thereof in a sample that comprises:

(i) Contacting the sample with a polystyrene or a polycarbonate surface under suitable conditions for the binding of the apolipoprotein or the isoform thereof to the surface, wherein the surface contains no antibodies specific for said apolipoprotein or isoform thereof bound to it, (ii) Contacting the surface to which the apolipoprotein or the isoform thereof is bound formed in step (i) with an antibody specific for said apolipoprotein or for said isoform thereof under suitable conditions for the formation of a complex between the antibody and the apolipoprotein or the isoform thereof, and (iii) Detecting the complexes formed in step (ii), wherein the polystyrene surface or the polycarbonate surface is not treated before contacting the sample or is blocked with albumin prior to contacting the sample.

Apolipoproteins to be detected and/or quantified according to the first method of the invention include apoCI, apoAIV, apoCI, apoCII, apoCIII, apoE and apoJ (clusterin). Apolipoprotein isoforms to be detected and/or quantified include apoCI, apoAIV, apoCI, apoCII, apoCIII, apoE and apoJ (clusterin) isoforms. In a particular embodiment, the apolipoprotein to be detected and/or quantified according to the first method of the invention is apoE. In a particular embodiment, apolipoprotein isoforms to be detected and/or quantified according to the first method of the invention are apoE isoforms selected from the group consisting of apoE2, apoE3 and apoE4. In a more particular embodiment, the apolipoprotein is apoE, and more particularly, the apolipoprotein isoform is apoE4.

Thus, in a first step of the first method of the invention, a sample is contacted with a polystyrene surface or a polycarbonate surface under suitable conditions for the binding of the apolipoprotein or the isoform thereof in the sample to said polystyrene surface or said polycarbonate surface, wherein said surface contains no antibodies specific for said apolipoprotein or isoform thereof bound to it.

Contacting between the sample and the polystyrene surface or a polycarbonate surface may be performed by direct contact under suitable conditions for the binding of the apolipoprotein or isoform thereof in the sample to the polystyrene surface or to the polycarbonate surface. As the skilled person understands, said conditions will be suitable conditions for interactions between the apolipoprotein or isoform thereof and the polystyrene or polycarbonate surface, preferably suitable conditions for electrostatic and/or hydrophobic interactions between the apolipoprotein or isoform thereof and the polystyrene surface or the polycarbonate surface. In a particular preferred embodiment, the surface is a polystyrene surface. Suitable conditions for the binding may be determined by the skilled person and include appropriate temperature, time of incubation, pH, sample concentration, etc. In a particular embodiment, the temperature ranges from 4 to 40° C., in particular from 10 to 35° C., more particularly from 15 to 30° C., preferably from 20 to 25° C. (room temperature). In a particular embodiment, the pH during said contacting step ranges from pH 2 to pH 10, preferably from pH 4 to pH 10. In a particular embodiment, the sample is incubated in contact with the surface, preferably the polystyrene surface, for at least 1 minute, preferably for at least 5 minutes, more preferably for at least 30 minutes, even more preferably for at least 60 minutes. Apolipoprotein-containing samples according to the invention may be put into contact with the surface, preferably a polystyrene surface, without being previously diluted or diluted, wherein dilution is at least 1:2, preferably at least 1:5, more preferably at least 1:10, even more preferably at least 1:100, even more preferably at least 1:200. As the skilled person understands, different buffers are suitable for dilution of the sample. In a particular sample, dilution of the sample is performed in phosphate-buffered saline (PBS) or in carbonate/bicarbonate buffer, more preferably in PBS.

In a particular embodiment, the binding of the apolipoprotein or the isoform thereof and the polystyrene or polycarbonate surface is not mediated by any peptide, any polypeptide, any lipid or any cross-linking agent. In particular, said peptide not mediating the binding is a peptide able to bind an apolipoprotein or isoform thereof and includes, without limitation, amyloid peptides. Amyloid peptides include, without limitation, amyloid precursor protein (APP), β-amyloid peptides [peptides of 36-43 amino acids that are crucially involved in Alzheimer's disease as the main component of the amyloid plaques found in the brains of Alzheimer patients, including Aβ(1-5), Aβ(1-6), Aβ(1-12), Aβ(1-40), Aβ(1-42), Aβ(12-28), Aβ(13-28), Aβ(25-35), Aβ(35-42), Aβ(33-42) and Aβ(33-40), wherein the expression Aβ(X-Y) refers to a peptide derived from the beta-amyloid peptide consisting of the amino acids at position X to the amino acid at position Y), Aβ40, and Aβ42].

Lipids not mediating the binding include, without limitation, phospholipids, and fatty acids.

In a particular embodiment, the sample containing the apolipoprotein or isoform thereof to be determined and/or quantified is a biological sample. Biological samples according to the invention include, without limitation, biological fluids such as blood, plasma, serum, urine, saliva, urine, and cerebrospinal fluid (CSF). Methods for isolating samples are well known to those skilled in the art. In a particular embodiment, the sample is a plasma sample. Suitable dilutions of a plasma sample according to the first method of the invention range from 1:10 to 1:100000, preferably from 1:100 to 1:1000, more preferably the dilution of the plasma sample is 1:200.

The polystyrene or polycarbonate surface, preferably polystyrene surface, according to the invention does not contain any antibody specific for the apolipoprotein or isoform thereof bound to it and for which detection and/or the quantification is performed. Polystyrene surfaces according to the invention include any polystyrene surface susceptible of being contacted with a sample, particularly a biological sample, and include, without limitation, plates, tubes, beads, and arrays, all of them commercially available and, in general, any polystyrene surface suitable for microfluidic-based assays. In a particular embodiment, the polystyrene surface is comprised by an ELISA plate, turbidimetric beads, luminex beads or, in general, by any polystyrene surface suitable for microfluidic-based assays. Polycarbonate surfaces according to the invention include any polystyrene surface susceptible of being contacted with a sample, particularly a biological sample, and include, without limitation, plates, tubes, beads, and arrays, all of them commercially available. In any case, said polystyrene surface or polycarbonate surface does not contain antibodies which are specific for the apolipoprotein or isoform thereof to be bound to said surface.

Polystyrene plates according to the invention include ELISA polystyrene plates commercially available from Nunc, Fisher Scientific, VWR, Greiner, and Corning, by way of example.

Polystyrene beads according to the invention include, without limitation, beads commercially available from Sigma Aldrich. In a particular embodiment, the polystyrene beads have a mean particle size ranging from 50 nm to 1 μm, preferably from 100 nm to 500 nm, more preferably from 150 nm to 400 nm, even more preferably from 200 to 300 nm. In a particular embodiment, the polystyrene beads are amine-modified polystyrene beads. In a particular alternative embodiment, the polystyrene beads are carboxylate-modified polystyrene beads. Polystyrene beads according to the invention include, without limitation, Luminex® beads and turbidimetric beads. Luminex beads are microspheres commercially available from Luminex.

In a particular embodiment, the polystyrene surface or the polycarbonate surface is not treated before contacting with the sample. In an alternative preferred embodiment, the polystyrene surface or the polycarbonate surface is blocked before contacting with the sample, that is to say, the polystyrene surface or the polycarbonate surface is blocked prior to the binding step (i) of the first method of the invention. In a particular embodiment, the polystyrene surface or the polycarbonate surface is blocked prior to the binding step by a protein other than an apolipoprotein and/or by a detergent. Suitable proteins for blocking the surface, preferably a polystyrene surface, prior to the binding step include, without limitation, albumin such as bovine serum albumin (BSA), casein, and gelatin, as well as commercially available blocking solutions such as Superblock (Pierce). Particularly preferred proteins for the blocking are BSA, casein and gelatin, more preferably, BSA, even more preferably, BSA ranging from 1% to 3%, more preferably BSA 1%. In a particular embodiment, the polystyrene surface or the polycarbonate surface is blocked with albumin prior to contacting the sample, more preferably the albumin is BSA. In a particular embodiment, the surface is blocked by BSA 1%. Additionally or alternatively to the protein other than an apolipoprotein, the surface, preferably a polystyrene surface, is blocked prior to the binding step by a detergent. Suitable detergents for blocking the polystyrene surface prior to the binding step include, without limitation, polyvinylpyrolidone-40 (PVP-40), polysorbate 20 (Tween 20), Nonidet-P40, and Triton X-100. In a particular embodiment, the detergent is polysorbate 20. In a particular embodiment, the surface is blocked by polysorbate 20.

In an embodiment of the invention, the polystyrene or polycarbonate, preferably polystyrene, surface is treated with a washing solution after contacting with a sample, that is to say, the surface is treated with a washing solution after the binding step (i) of the first method of the invention. Preferably, the treatment of the surface with the washing solution is performed after the binding step (i) and before the step (ii) of the first method of the invention. In a particular embodiment, the washing solution contains one or more salts. Preferably, the salt contained by the washing solution is NaCl, comprised by a Tris buffer (TBS) or by a phosphate buffer (PBS). Additionally or alternatively, the washing solution contains at least one detergent. Preferably, the detergent is selected from the group consisting of polysorbate 20 (Tween 20) and Triton X-100. Additionally or alternatively, the washing solution contains an acid. Preferably, the acid is selected from the group consisting of HCl and formic acid. More preferably, the acid is selected from HCl 2M and formic acid 70%. Additionally or alternatively, the washing solution contains a base. Preferably, the base is NaOH, more preferably NaOH 2M. Additionally or alternatively, the washing solution contains a reducing agent. Preferably, the reducing agent is 2-mercaptoethanol. Additionally or alternatively, the washing solution does not contain an enzymatic detergent (such as a protease), an oxidizing reagent (such as sodium hypochlorite) or the combination thereof.

In a second step of the first method of the invention, the polystyrene or polycarbonate, preferably polystyrene, surface to which the apolipoprotein or isoform thereof is bound, as a result of the first step of the method, is contacted with an antibody specific for said apolipoprotein or isoform thereof bound to the polystyrene or polycarbonate surface. This step is performed under suitable conditions for the formation of a complex between the antibody and the apolipoprotein or isoform thereof bound to the polystyrene or polycarbonate surface.

Apolipoprotein-specific antibodies are known by the skilled person and commercially available. Exemplary, non-limiting, antibodies that can be used in the context of the invention include the following:

for apoAI detection and/or quantification: rabbit polyclonal antibody for apoAI from Santa Cruz Biotechnology (FL-267, catalog number #sc-30089), mouse monoclonal anti-apoAI antibody from Santa Cruz Biotechnology (069-01, catalog number #sc-58230), mouse monoclonal anti-apoAI antibody from Santa Cruz Biotechnology (B10, catalog number #sc-376818), rabbit polyclonal anti-apoAI antibody from Abcam (catalog number #ab64308), and goat polyclonal anti-apoAI antibody from Abcam (catalog number #ab7613).

for apoAII detection and/or quantification: mouse monoclonal anti-apoAII antibody from LifeSpan Biosciences (catalog number #LS-B4281), and rabbit polyclonal anti-apoAII antibody from OriGene (catalog number #TA328111).

for apoAIV detection and/or quantification: goat polyclonal anti-human apoAIV from Abcam (catalog number #ab59036), and rabbit polyclonal anti-human apoAIV from Sigma-Aldrich (catalog number #HPA001352).

for apoCI detection and/or quantification: rabbit polyclonal anti-apoCI antibody from Abcam (catalog number #ab20793), and goat polyclonal anti-apoCI antibody from Abcam (catalog number #ab104446).

for apoCII detection and/or quantification: rabbit polyclonal anti-apoCII antibody from Abcam (catalog number #ab76452), rabbit polyclonal anti-apoCII antibody from Sigma-Aldrich (catalog number #SAB1300917), and mouse monoclonal anti-apoCII antibody from Novus-Biologicals (3E4, catalog number #H00000344-M01).

for apoCIII detection and/or quantification: goat polyclonal anti-apoCIII antibody from Abcam (catalog number #ab7619), and rabbit polyclonal anti-apoCIII antibody from Sigma-Aldrich (catalog number #A0734).

for apoE detection and/or quantification: rabbit polyclonal antibody for total apoE (SantaCruz Biotechnology, Inc., #sc-98573), and rabbit IgG anti-human apoE from TaKaRa Clontech (catalog numbers #18171A and #18171B), and rabbit polyclonal anti-human apoE antibody from Abcam (catalog number #ab72398).

for apoE2 isoform detection and/or quantification: mouse monoclonal anti-human apoE2 from Biolegend (3C2 clone, catalog number #815001; clone 8G3, catalog number #812701).

for apoE3 isoform detection and/or quantification: rabbit polyclonal anti-human apoE3 from Preprotech (catalog number #350-02).

for apoE4 isoform detection and/or quantification: mouse monoclonal anti-human apoE4 from Merck Millipore (clone 4E4, catalog number #MABN43), mouse monoclonal anti-human apoE4 from BioLegend (clone 5B5, catalog number #811601), mouse monoclonal antibody specific for apoE E4, clone 4E4 (Novus Biologicals, #NBP1-49529), mouse monoclonal antibody specific for apoE E4, clone 5B5 (IBL #10025), mouse monoclonal antibody specific for apoE E4, clone 1F9 (MBL, #M067-3), and mouse monoclonal antibody anti-apoE4, clone 4E4 from Thermo Scientific (catalog number #MA5-16146).

for apoJ detection and/or quantification: mouse monoclonal anti-apoJ antibody from Abcam (CLI-9, catalog number #ab16077), and goat polyclonal anti-apoJ antibody from Sigma-Aldrich (catalog number #SAB2500251).

Contacting between the surface to which the apolipoprotein or isoform thereof is bound as a result of step (i) with an antibody specific for said apolipoprotein or isoform thereof is performed under suitable conditions for the formation of a complex between the antibody and the apolipoprotein or isoform thereof. Suitable conditions for the formation of said complex may be determined by the skilled person and include appropriate temperature, time of incubation, and pH. In a particular embodiment, the temperature ranges from 4 to 40° C., in particular from 10 to 35° C., more particularly from 15 to 30° C., preferably from 20 to 25° C. (room temperature). In a preferred embodiment, the temperature in steps (i) and (ii) of the first method of the invention is substantially the same. In a particular embodiment, the pH ranges from pH 2 to pH 10, preferably from pH 4 to pH 10. In a preferred embodiment, the pH in steps (i) and (ii) of the first method of the invention is substantially the same. In a particular embodiment, the antibody is incubated with the apolipoprotein or isoform thereof bound the surface for at least 1 minute, preferably for at least 5 minutes, more preferably for at least 30 minutes, even more preferably for at least 60 minutes.

In a third step of the first method of the invention, complexes between the apolipoprotein or isoform thereof bound to the polystyrene or polycarbonate surface and the specific antibody for said apolipoprotein or isoform thereof, as a result of the second step of the method, are detected.

Since the apolipoprotein, or isoform thereof, is not a detectable molecule by itself, the detection step is performed, in a particular embodiment, by means of a detectable molecule or complex. The complex apolipoprotein-antibody or apolipoprotein isoform-antibody may be detected by different methods known by the skilled person. In a particular embodiment of the invention, detection of the complex apolipoprotein-antibody or the complex apolipoprotein isoform-antibody is performed by means of a detectable reagent which binds specifically to the complex apolipoprotein-antibody or the complex apolipoprotein isoform-antibody, wherein the detectable reagent facilitates the detection of the complex by generating a signal which can be measured. Methods for labeling biological molecules, such as polypeptides and antibodies, are well-known in the art.

Any of a wide variety of detectable reagents can be used in the practice of the present invention. Suitable detectable reagents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

Detectable reagents for optical imaging include, for example, fluorescein, a fluorescein derivative, indocyanine green, Oregon green, a derivative of Oregon green, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye, and various other fluorescent compounds, such as Cy3, Cy2, Cy5, the Alexa Fluor® fluorescent label family (Molecular Probes, Inc.), carboxyfluorescein (FAM) and fluorescein isothiocyanate (FITC).

In a particular embodiment, the detectable reagent is a protein. The term "protein", in the context of the present invention, refers to macromolecules consisting of one or more amino acid chains. The proteins are responsible for carrying out a diverse group of cell functions based on their ability to specifically bind other molecules. The proteins can be bound to other proteins as well as to small substrate molecules. Non-limiting examples of proteins suitable as detectable reagents include, without limitation, enzymes, fluorescent proteins, luminescent proteins and antigens.

In a preferred embodiment, the protein is an enzyme. The term "enzyme", in the context of the present invention, refers to a protein working as a highly selective catalyst, accelerating both the speed and the specificity of the metabolic reaction for which it is specific. Non-limiting examples of enzymes suitable for the invention include, without limitation, horseradish peroxidase (HRP) and alkaline phosphatase. As the person skilled in the art will understand, the enzymes suitable for use in the present invention are indirectly detectable as a result of their capability of catalyzing modifying a substrate in a compound detectable by colorimetry, chemiluminescence or fluorimetry. Examples of suitable substrates include, without limitation, p-nitrophenyl phosphate (PNPP), 2,2'-azinobis[3-ethylbenzothiazolin-6-sulfonic acid] (ABTS), o-phenylenediamine (OPD), and 3,3',5,5'-tetramethylbenzidine (TMB).

Bioluminescent proteins or photoproteins are a particular case of oxidative enzymes capable of carrying out a chemical reaction of their specific prosthetic groups, resulting in light emission without requiring prior excitation. Non-limiting examples of bioluminescent proteins include firefly luciferase, *Renilla luciferase* and aequorin.

In another embodiment, the protein is a fluorescent protein. The term "fluorescent protein", in the context of the present invention, refers to a protein with the capability of emitting light when it is excited at a wavelength suitable for excitation. Non-limiting examples of fluorescent proteins that can be used in the complex of the invention include, without limitation, GFP, GFPuv, BFP, CFP, YFP, EBFP2, mCerulean, mCerulean3, mVenus, mTurquoise, T-Sapphire, citrine, amFP486, zFP506, zFP538, drFP, DsRed, mCherry, dTomate, mTFP1, TagRFP-T, mKO2, mRuby, mKate, mAmetrine, REACh, R-phycoerythrin (R-PE) and Allophycocyanin (APC).

In another embodiment, the protein is a luminescent protein. The term "luminescent protein", in the context of the present invention, refers to a protein capable of emitting light when it is excited at a wavelength suitable for excitation.

In another embodiment, the protein is an antigen. The term "antigen", in the context of the present invention, refers to a molecule that induces an immune response in the body. Therefore, an antigen can be used for generating an antibody that recognizes it and binds specifically to it. Non-limiting examples of antigens include, inter alia, tumor antigens, such as the carcinoembryonic antigen (CEA), HER2, prostate specific antigen (PSA) and tissue plasminogen activator and its recombinant variants, such as Activase®, as well as bacterial antigens, allergens, etc. As the person skilled in the art will understand, the antigens suitable for use in the present invention are indirectly detectable as a result of their capability of being specifically recognized by an antibody.

In another embodiment, the detectable reagent is a haptene. The term "haptene", in the context of the present invention, refers to a group of chemical compounds having a small molecular size (<10,000 Da) which are antigenic but unable to induce by themselves an specific immune reaction. The chemical coupling of a haptene to a large immunogenic protein, called carrier, generates an haptene-immunogenic carrier conjugate which is able to induce a specific immune reaction. Non-limiting examples of vitamins include biotin (vitamin B7), digoxigenin, dinitrophenol (DNP) and nitroiodophenol (NIP). In a particular embodiment, the vitamin is biotin. The term "biotin", in the context of the present invention, refers to a water- and alcohol-soluble heat-stable vitamin, also referred to as vitamin H and vitamin B7, characterized by specifically binding to avidin with the highest affinity described to date of Kd=10-15 M. As the person skilled in the art will understand, biotin is indirectly detectable as a result of its capability of being specifically recognized by avidin or variants thereof, such as streptavidin and neutravidin.

Detection of the detectable reagent may be performed by means of fluorimetry or colorimetry using apparatuses suitable for the type of reagents and the type of sample, which are known by the person skilled in the art.

By way of example, the complex apolipoprotein-antibody, wherein the apolipoprotein of the complex is attached to the surface, preferably a polystyrene surface, is incubated with a second antibody (reporter antibody) that is specific for the anti-apolipoprotein antibody previously complexed with the apolipoprotein. Therefore, in a particular embodiment of the first method of the invention, detection of complexes apolipoprotein-antibody formed in step (ii) of the method are detected by means of a reporter antibody which is specific for the anti-apolipoprotein antibody. In a particular embodiment, the anti-apolipoprotein antibody and the reporter antibody are the same antibody. In a preferred embodiment, the second antibody (reporter antibody) is conjugated with an enzyme, in conditions similar to the conditions of incubation of the surface with the apolipoprotein and/or of incubation of the antibody specific for the apolipoprotein with the apolipoprotein bound to the surface. The complexes antibody-apolipoprotein bound to the surface are detected with the addition of a substrate that is converted by the enzyme into a detectable product, for example, by means of fluorimetry in a fluorescence microscope or by colorimetry in a spectrophotometer. In an alternative embodiment, detection can be done in an analogous manner by means of the use of a probe specific for the apolipoprotein suitably labeled with a detectable reagent.

Thus, according to the present invention, the apolipoprotein-antibody complex, or the apolipoprotein isoform-antibody complex, may be detected by means of a detectable molecule or complex, as described above. In an alternative embodiment of the invention, the complex apolipoprotein-antibody or apolipoprotein isoform-antibody is detected by turbidimetry, particularly by means of an immunoturbidimetric assay. Formation of a complex apolipoprotein-antibody or a complex apolipoprotein isoform-antibody, when said apolipoprotein or apolipoprotein isoform is present in the sample to be analysed, results in an increase of turbidity compared to turbidity in a sample lacking the apolipoprotein or apolipoprotein isoform, wherein said turbidity variation can be measured (for example, by means of a spectrophotometer). In a preferred embodiment of the invention, the immunoturbidimetric assay is LEIT (Latex-Enhanced Immunoturbidimetry Technology).

In a particular embodiment, complex detection is performed by ELISA. In an alternative embodiment, complex detection is performed by an immunoturbidimetric assay.

Method for the Determination of the Relative Amounts of an Apolipoprotein Isoform The inventors of the present invention have developed a method to determine whether a particular apolipoprotein isoform is present or not in a subject based on a double ELISA assay for a plasma sample from the subject, wherein one assay determines the levels of the particular apolipoprotein isoform and the other assay determines the levels of total apolipoprotein. The ratio apolipoprotein isoform/total apolipoprotein is then calculated. See Example 1, "Discrimination of the heterozygous/homozygous APOE ε4 carriers in plasma samples", and FIG. 4. Apolipoprotein isoform content of apoE has also been determined by an immunoturbidimetric assay. See Example 2, "ApoE4 detection by a turbidimetric assay".

Thus, in another embodiment, the present invention relates to an in vitro method for determining the relative amount of an isoform of a given apolipoprotein with respect to the total content of said apolipoprotein in a sample (second method of the invention) that comprises:

(i) Contacting the sample with a polystyrene or a polycarbonate surface under suitable conditions for the binding of the apolipoprotein to the surface, wherein the surface contains no antibodies specific for said apolipoprotein bound to it, (ii) Contacting the surface to which the apolipoprotein is bound formed in step (i) with a first antibody specific for said apolipoprotein isoform and with a second antibody which is capable of binding to all the isoforms of said apolipoprotein present in the sample, wherein said contacting is carried out under conditions suitable for the formation of a first complex comprising the first antibody and the apolipoprotein isoform and for the formation of a second complex comprising the second antibody and all the isoforms of said apolipoprotein, (iii) Detecting the first and second complexes formed in step (ii) and (iv) Determining the relative amounts of the isoform with respect to the total apolipoprotein content based on the levels of the first and second complex obtained in step (iii).

In a particular embodiment, the invention relates to an in vitro method for determining the relative amount of an isoform of a given apolipoprotein selected from the group consisting of apoAI, apoAIV, apoCI, apoCII, apoCIII, apoE and apoJ (clusterin) with respect to the total content of said apolipoprotein in a sample that comprises:

(i) Contacting the sample with a polystyrene or a polycarbonate surface under suitable conditions for the binding of the apolipoprotein to the surface, wherein the surface contains no antibodies specific for said apolipoprotein bound to it, (ii) Contacting the surface to which the apolipoprotein is bound formed in step (i) with a first antibody specific for said apolipoprotein isoform and with a second antibody which is capable of binding to all the isoforms of said apolipoprotein present in the sample, wherein said contacting is carried out under conditions suitable for the formation of a first complex comprising the first antibody and the apolipoprotein isoform and for the formation of a second complex comprising the second antibody and all the isoforms of said apolipoprotein, (iii) Detecting the first and second complexes formed in step (ii) and (iv) Determining the relative amounts of the isoform with respect to the total apolipoprotein content based on the levels of the first and second complex obtained in step (iii)

wherein the polystyrene surface or the polycarbonate surface is not treated before contacting the sample or is blocked with albumin prior to contacting the sample Apolipoprotein isoforms to be determined according to the second method of the invention include apoAI, apoAIV, apoCI, apoCII, apoCIII, apoE and apoJ (clusterin) isoforms. In a particular embodiment, the apolipoprotein isoforms to be determined are apoE isoforms selected from the group consisting of apoE2, apoE3 and apoE4, preferably apoE4. In a more particular embodiment, the apolipoprotein is apoE and the apolipoprotein isoform is apoE4.

In a first step of the second method of the invention, a sample is contacted with a polystyrene or a polycarbonate surface under suitable conditions for the binding of the apolipoprotein or the isoform thereof in the sample to the surface, wherein said surface contains no antibodies specific for said apolipoprotein or isoform thereof bound to it.

Suitable conditions for the binding of an apolipoprotein or isoform thereof in a sample to a polystyrene or a polycarbonate, preferably polystyrene, surface have been described previously in the context of the first method of the invention and incorporated herein.

In a particular embodiment, the sample containing the apolipoprotein or isoform thereof to be determined is a biological sample. Suitable biological samples have been mentioned in the context of the first method of the invention and incorporated herein. Preferred samples include biological fluids such as blood, plasma, serum, urine, saliva, urine, and cerebrospinal fluid (CSF). In a particular embodiment, the sample is a plasma sample. Suitable dilutions of a plasma sample range from 1:10 to 1:100000, preferably from 1:100 to 1:1000, more preferably the dilution of the plasma sample is 1:200.

The polystyrene or polycarbonate surface according to the invention does not contain any antibody specific for the apolipoprotein or isoform thereof bound to it and for which detection is performed. Polystyrene or polycarbonate surfaces according to the invention have been mentioned above and incorporated herein. In a particular embodiment, the polystyrene surface is comprised by an ELISA plate, luminex beads or turbidimetric beads. In any case, said polystyrene or polycarbonate surface does not contain antibodies which are specific for the apolipoprotein or isoform thereof to be bound to said surface.

In a particular embodiment, the polystyrene or polycarbonate surface according to the second method of the invention is formed by an only entity, so that said only entity provides the surface necessary for the binding of the apolipoprotein, e.g. a single plate such as a single ELISA plate or a single well in an ELISA plate. It will be understood that this embodiment can be used in those cases wherein the first and second antibodies are detected using different detectable markers, so that the signal resulting from each antibody can be determined precisely without interferences by the signal provided by the second antibody. In an alternative embodiment, the polystyrene or polycarbonate surface according to the second method of the invention is formed by a plurality of entities, that is to say, by at least two units of the entity providing the surface available for the binding of the apolipoprotein to said surface, e.g. a plurality of beads such as luminex beads or turbidimetric beads. In a particular embodiment of the second method of the invention, the polystyrene or polycarbonate surface to be contacted with a sample under suitable conditions for the binding of the apolipoprotein in said sample to the surface is formed by a plurality of entities. Preferably, said surface is formed by luminex beads or by turbidimetric beads. This embodiment is useful when the complexes formed in step (i) are not further treated with detectable reagents which allow distinguishing both antibodies by the signal provided by each detectable reagent. For instance, in the case of the turbidimetric detection, the formation of the complex between the apolipoprotein and the antibody is detected by an increase in the turbidity of the sample. In this case, it is not possible to determine whether the increased in the turbidity is due to the formation of complexes of the apolipoprotein isoform and the first antibody or to the complexes of the total apolipoprotein and the second antibody. In this case, the contacting has to be done using a surface that is formed by a plurality of entities (e.g. in the form of microparticles), so that the entities contacted with each type of antibody can be separately detected by placing them in different containers.

In a particular embodiment, the polystyrene or polycarbonate surface is not treated before contacting with the sample. In an alternative preferred embodiment, the polystyrene or polycarbonate surface is blocked before contacting with the sample, that is to say, the surface is blocked prior to the binding step (i) of the second method of the invention. In a particular embodiment, the polystyrene or polycarbonate surface is blocked prior to the binding step by a protein other than an apolipoprotein and/or by a detergent. Suitable proteins and detergents for blocking the surface according to the invention have been described above and incorporated herein by reference. Particularly preferred proteins for the blocking are BSA, casein and gelatin, more preferably, BSA, even more preferably, BSA ranging from 1% to 3%, more preferably BSA 1%. Suitable detergents for blocking the surface prior to the binding step include, without limitation, polyvinylpyrolidone-40 (PVP-40), polysorbate 20 (Tween 20), Nonidet-P40, and Triton X-100.

In a particular embodiment, the polystyrene or polycarbonate surface is treated with a washing solution after contacting with a sample, that is to say, the polystyrene or polycarbonate surface is treated with a washing solution after the binding step (i) of the second method of the invention. Preferably, the treatment of the polystyrene or polycarbonate surface with the washing solution is performed after the binding step (i) and before the step (ii) of the second method of the invention. Suitable washing solutions have been described previously and incorporated herein. In a particular embodiment, the washing solution contains one or more salts. Preferably, the salt contained by the washing solution is NaCl. Additionally or alternatively, the washing solution contains at least one detergent. Preferably, the detergent is selected from the group consisting of polysorbate 20 (Tween 20) and Triton X-100. Additionally or alternatively, the washing solution contains an acid. Preferably, the acid is selected from the group consisting of HCl and formic acid. More preferably, the acid is selected from HCl 2M and formic acid 70%. Additionally or alternatively, the washing solution contains a base. Preferably, the base is NaOH, more preferably NaOH 2M. Additionally or alternatively, the washing solution contains a reducing agent. Preferably, the reducing agent is 2-mercaptoethanol. Additionally or alternatively, the washing solution does not contain an enzymatic detergent (such as a protease), an oxidizing reagent (such as sodium hypochlorite) or the combination thereof.

In a second step of the second method of the invention, the surface to which the apolipoprotein is bound formed in step (i) is contacted with a first antibody specific for said apolipoprotein isoform and with a second antibody which is capable of binding to all the isoforms of said apolipoprotein present in the sample, wherein said contacting is carried out under conditions suitable for the formation of a first complex comprising the first antibody and the apolipoprotein isoform and suitable for the formation of a second complex comprising the second antibody and all the isoforms of said apolipoprotein.

Antibodies specific for apolipoproteins and antibodies specific for particular apolipoproteins isoforms have been cited above in the context of the first method of the invention and incorporated herein.

According to the second method of the invention, the surface to which the apolipoprotein is bound formed in step (i) is contacted with a first antibody and with a second antibody, wherein the first antibody is specific for the apolipoprotein isoform to be determined and wherein the second antibody is capable of binding to all the isoforms of said apolipoprotein. In a particular embodiment, the surface to which the apolipoprotein is bound and that is contacted with the first antibody is the same surface to which the apolipoprotein is bound and contacted with the second antibody, that is to say, the contact is performed in a single container, for example, a single well in a plate such as an ELISA plate. Therefore, the contact between the surface to which the apolipoprotein is bound and the first antibody is performed in the same container as the one wherein the contact with a second antibody is performed. In an alternative embodiment, a first surface to which the apolipoprotein is bound is contacted with the first antibody and a second surface to which the apolipoprotein is bound is contacted with the second antibody, wherein said first and second surfaces are different surfaces, as a way of example, different wells in a plate (such as an ELISA plate), different beads (such as luminex beads of turbidimetric beads) or different particles. Therefore, the contact between the surface to which the apolipoprotein is bound and the first antibody is performed in a different container from the container wherein the contact between the surface to which the apolipoprotein is bound and the second antibody is performed, that is to say, separate containers are used. In a more particular embodiment, when separate containers are used, each of said containers comprises a plurality of entities, e.g. two separate sets of beads (such as luminex beads of turbidimetric beads) or two separate set of particles.

In a preferred embodiment of the second method of the invention, the surface used in step (i) is formed by a plurality of entities, and the contacting with the first antibody and with the second antibody in step (ii) is performed in separate containers, each containing part of the plurality of entities forming the surface.

Contacting between the surface to which the apolipoprotein isoform is bound as a result of step (i) with a first antibody specific for said apolipoprotein isoform and with a second antibody which is capable of binding to all the isoforms of said apolipoprotein thereof is performed under suitable conditions for the formation of a first complex comprising the first antibody and the apolipoprotein isoform and for the formation of a second complex comprising the second antibody and all the isoforms of said apolipoprotein. Suitable conditions for the formation of said complexes may be determined by the skilled person and include appropriate temperature, time of incubation, and pH. In a particular embodiment, the temperature ranges from 4 to 40° C., in particular from 10 to 35° C., more particularly from 15 to 30° C., preferably from 20 to 25° C. (room temperature). In a preferred embodiment, the temperature in steps (i) and (ii) of the second method of the invention is substantially the same. In a particular embodiment, the pH ranges from pH 2 to pH 10, preferably from pH 4 to pH 10. In a preferred embodiment, the pH in steps (i) and (ii) of the second method of the invention is substantially the same. In a particular embodiment, the first antibody is incubated with the apolipoprotein isoform to be determined bound the surface for at least 1 minute, preferably for at least 5 minutes, more preferably for at least 30 minutes, even more preferably for at least 60 minutes. In a particular embodiment, the second antibody is incubated with the isoforms of the apolipoprotein to be determined bound the surface for at least 1 minute, preferably for at least 5 minutes, more preferably for at least 30 minutes, even more preferably for at least 60 minutes.

In a third step of the second method of the invention, first and second complexes formed in the second step of the method are detected.

As previously described, the surface to which the apolipoprotein is bound and that is contacted with the first antibody may be the same as or different from the surface to which the apolipoprotein is bound and contacted with the second antibody. In a particular embodiment, when said surfaces are different surfaces and contacting is performed in separate containers, the detection in step iii) of the second method of the invention is performed separately in each container.

In a preferred embodiment of the second method of the invention, the surface used in step (i) is formed by a plurality of entities, the contacting with the first antibody and with the second antibody in step (ii) is performed in separate containers, each containing part of the plurality of entities forming the surface, and the detection in step (iii) is carried out separately in each container. This embodiment is particularly preferred when the polystyrene of polycarbonate surfaces are comprised by beads, preferably luminex beads or turbidimetric beads, and detection is performed by means of immunoturbidimetry. Thus, according to this embodiment of the invention, first and second complexes formed in the second step of the method are detected by turbidimetry, particularly by means of an immunoturbidimetric assay. Formation of a complex apolipoprotein (all isoforms thereof)-antibody or a complex apolipoprotein isoform-antibody, when said apolipoprotein or apolipoprotein isoform is present in the sample to be analysed, results in an increase of turbidity compared to turbidity in a sample lacking the apolipoprotein or apolipoprotein isoform, wherein said turbidity variation can be measured (for example, by means of a spectrophotometer). In a preferred embodiment of the invention, the immunoturbidimetric assay is LEIT.

In a particular alternative embodiment, first and second complexes formed in the second step of the method are detected by means of a detectable reagent. Suitable detectable reagents in the context of the invention have been described previously in the context of the first method of the invention and incorporated herein. In a preferred embodiment, first and second complexes formed in the second step of the method are detected by means of a reporter antibody, which is specific for the anti-apolipoprotein antibody and/or the anti-apolipoprotein isoform antibody. In a preferred embodiment, the second antibody (reporter antibody) is conjugated with an enzyme, in conditions similar to the conditions of incubation of the surface with the apolipoprotein isoform and/or of incubation of the antibody specific for the apolipoprotein isoform with the apolipoprotein isoform bound to the surface. This embodiment is particularly preferred when the polystyrene of polycarbonate surfaces are comprised by a plate, preferably an ELISA plate, and when detection is performed by means of an ELISA assay.

In a fourth step of the second method of the invention, the relative amounts of the isoform with respect to the total apolipoprotein content based on the levels of the first and second complex obtained in step (iii) are determined.

In a particular embodiment, the ratio between the signals derived from the detection of the first and second complexes detected in step (iii) of the second method of the invention is calculated. As a result, the relative amount of an isoform of a particular apolipoprotein with respect to the total content of said apolipoprotein is determined. As the skilled person acknowledges, the ratio may range between 0 (when the particular apolipoprotein isoform is absent in the sample to be analyzed), and 1 (when the particular apolipoprotein isoform is the only isoform of said apolipoprotein present in the sample to be analised).

Allelic Dosage Determination Method of the Invention

The inventors of the present invention have developed a method to determine whether a subject is an homozygous or heterozygous carrier for a particular apolipoprotein isoform based on a double assay of a sample the subject, wherein one assay determines the levels of the particular apolipoprotein isoform and the other assay determines the levels of the total apolipoprotein. The ratio apolipoprotein isoform/total apolipoprotein is then calculated and, from this ratio, the allelic dosage can be inferred. See Example 1. Apolipoprotein isoform content has also been determined by an immunoturbidimetric assay. See Example 2.

Thus, in a further aspect, the invention relates to a method for determining the allelic dosage of haplotypes associated with the expression of an apolipoprotein isoform in a subject (third method of the invention) that comprises:

(i) Contacting a protein-containing sample from said subject derived from a tissue wherein the apolipoprotein isoform is expressed with a polystyrene or polycarbonate surface under suitable conditions for the binding of the apolipoprotein isoform to the surface, wherein the surface contains no antibodies specific for said apolipoprotein isoform bound to it, (ii) Contacting the surface to which the apolipoprotein is bound formed in step (i) with at least one antibody specific for the apolipoprotein isoform under suitable conditions for the formation of a complex between the antibody and the apolipoprotein isoform, (iii) Determining the allelic dosage of the apolipoprotein isoform by correlating the amount of complex formed in step (ii) with the number of alleles encoding said genetic variant.

In a particular embodiment, the invention relates to a method for determining the allelic dosage of haplotypes associated with the expression of an apolipoprotein isoform of an apolipoprotein selected from the group consisting of apoCI, apoAIV, apoCI, apoCII, apoCIII, apoE and apoJ (clusterin) in a subject comprising, (i) Contacting a protein-containing sample from said subject derived from a tissue wherein the apolipoprotein isoform is expressed with a polystyrene or polycarbonate surface under suitable conditions for the binding of the apolipoprotein isoform to the surface, wherein the surface contains no antibodies specific for said apolipoprotein isoform bound to it, (ii) Contacting the surface to which the apolipoprotein is bound formed in step (i) with at least one antibody specific for the apolipoprotein isoform under suitable conditions for the formation of a complex between the antibody and the apolipoprotein isoform, (iii) Determining the allelic dosage of the apolipoprotein isoform by correlating the amount of complex formed in step (ii) with the number of alleles encoding said genetic variant wherein the polystyrene surface or the polycarbonate surface is not treated before contacting the sample or is blocked with albumin prior to contacting the sample.

Apolipoprotein isoforms to be determined according to the third method of the invention include apoCI, apoAIV, apoCI, apoCII, apoCIII, apoE and apoJ (clusterin) isoforms. In a particular embodiment, apolipoprotein isoforms to be determined according to the third method of the invention are apoE apolipoprotein isoforms selected from the group consisting of apoE2, apoE3 and apoE4. In a more particular embodiment, the apolipoprotein isoform to be determined according to the third method of the invention is apoE4.

In a first step of the third method of the invention, a protein-containing sample from a subject derived from a tissue wherein the apolipoprotein isoform is expressed is contacted with a polystyrene or a polycarbonate surface under suitable conditions for the binding of the apolipoprotein or the isoform thereof in the sample to the surface, wherein said surface contains no antibodies specific for said apolipoprotein or isoform thereof bound to it.

Suitable conditions for the binding of an apolipoprotein or isoform thereof in a sample to a polystyrene or a polycarbonate, preferably polystyrene, surface have been described previously in the context of the first method of the invention and incorporated herein.

The sample is a protein-containing sample derived from a tissue wherein the apolipoprotein isoform is expressed. Suitable samples include biological fluids such as blood, plasma, serum, urine, saliva, urine, and cerebrospinal fluid (CSF), as previously described. In a particular embodiment, the sample is a plasma sample. Suitable dilutions of a plasma sample range from 1:10 to 1:100000, preferably from 1:100 to 1:1000, more preferably the dilution of the plasma sample is 1:200.

The polystyrene or polycarbonate surface according to the invention does not contain any antibody specific for the apolipoprotein or isoform thereof bound to it and for which detection is performed. Polystyrene or polycarbonate surfaces according to the invention have been mentioned above and incorporated herein. In a particular embodiment, the polystyrene surface is comprised by an ELISA plate, luminex beads or turbidimetric beads. In any case, said polystyrene or polycarbonate surface does not contain antibodies which are specific for the apolipoprotein or isoform thereof to be bound to said surface.

In a particular embodiment, the polystyrene or polycarbonate surface according to the third method of the invention is formed by an only entity, so that said only entity provides the surface necessary for the binding of the apolipoprotein, e.g. a single plate such as a single ELISA plate. In an alternative embodiment, the polystyrene or polycarbonate surface according to the third method of the invention is formed by a plurality of entities, that is to say, by at least two units of the entity providing the surface available for the binding of the apolipoprotein to said surface, e.g. a plurality of beads such as luminex beads or turbidimetric beads. In a particular embodiment of the third method of the invention, the polystyrene or polycarbonate surface to be contacted with a sample under suitable conditions for the binding of the apolipoprotein in said sample to the surface is formed by a plurality of entities. Preferably, said surface is formed by luminex beads or by turbidimetric beads.

In a particular embodiment, the polystyrene or polycarbonate surface is not treated before contacting with the sample. In an alternative preferred embodiment, the polystyrene or polycarbonate surface is blocked before contacting with the sample, that is to say, the surface is blocked prior to the binding step (i) of the third method of the invention. In a particular embodiment, the polystyrene or polycarbonate surface is blocked prior to the binding step by a protein other than an apolipoprotein and/or by a detergent. Suitable proteins and detergents for blocking the surface according to the invention have been described above and incorporated herein. Particularly preferred proteins for the blocking are BSA, casein and gelatin, more preferably, BSA, even more preferably, BSA ranging from 1% to 3%, more preferably BSA 1%. Suitable detergents for blocking the surface prior to the binding step include, without limitation, polyvinylpyrolidone-40 (PVP-40), polysorbate 20 (Tween 20), Nonidet-P40, and Triton X-100.

In a particular embodiment, the polystyrene or polycarbonate surface is treated with a washing solution after contacting with a sample, that is to say, the polystyrene or polycarbonate surface is treated with a washing solution after the binding step (i) of the third method of the invention. Preferably, the treatment of the polystyrene or polycarbonate surface with the washing solution is performed after the binding step (i) and before the step (ii) of the third method of the invention. Suitable washing solutions have been described previously and incorporated herein. In a particular embodiment, the washing solution contains one or more salts. Preferably, the salt contained by the washing solution is NaCl. Additionally or alternatively, the washing solution contains at least one detergent. Preferably, the detergent is selected from the group consisting of polysorbate 20 (Tween 20) and Triton X-100. Additionally or alternatively, the washing solution contains an acid. Preferably, the acid is selected from the group consisting of HCl and formic acid. More preferably, the acid is selected from HCl 2M and formic acid 70%. Additionally or alternatively, the washing solution contains a base. Preferably, the base is NaOH, more preferably NaOH 2M. Additionally or alternatively, the washing solution contains a reducing agent. Preferably, the reducing agent is 2-mercaptoethanol. Additionally or alternatively, the washing solution does not contain an enzymatic detergent (such as a protease), an oxidizing reagent (such as sodium hypochlorite) or the combination thereof.

In a second step of the third method of the invention, the surface to which the apolipoprotein is bound formed in step (i) is contacted with at least one antibody specific for the apolipoprotein isoform under suitable conditions for the formation of a complex between the antibody and the apolipoprotein isoform.

In a particular preferred embodiment, the second step of the third method of the invention further comprises contacting the surface with a second antibody which is capable of binding to all the isoforms of said apolipoprotein present in the sample, wherein said contacting is carried out under conditions suitable for the formation of a first complex comprising the first antibody and the apolipoprotein isoform and for the formation of a second complex comprising the second antibody and all the isoforms of said apolipoprotein.

Antibodies specific for apolipoproteins and antibodies specific for particular apolipoproteins isoforms have been cited above in the context of the first method of the invention and incorporated herein.

Conditions suitable for the formation of a first complex comprising the first antibody and the apolipoprotein isoform and for the formation of a second complex comprising the second antibody and all the isoforms of said apolipoprotein may be determined by the skilled person and include appropriate temperature, time of incubation, and pH, as previously described. In a particular embodiment, the temperature ranges from 4 to 40° C., in particular from 10 to 35° C., more particularly from 15 to 30° C., preferably from 20 to 25° C. (room temperature). In a preferred embodiment, the temperature in steps (i) and (ii) of the third method of the invention is substantially the same. In a particular embodiment, the pH ranges from pH 2 to pH 10, preferably from pH 4 to pH 10. In a preferred embodiment, the pH in steps (i) and (ii) of the third method of the invention is substantially the same. In a particular embodiment, the first antibody is incubated with the apolipoprotein isoform to be determined bound the surface for at least 1 minute, preferably for at least 5 minutes, more preferably for at least 30 minutes, even more preferably for at least 60 minutes. In a particular embodiment, the second antibody is incubated with the isoforms of the apolipoprotein to be determined bound the surface for at least 1 minute, preferably for at least 5 minutes, more preferably for at least 30 minutes, even more preferably for at least 60 minutes.

In a particular embodiment, the surface to which the apolipoprotein is bound and that is contacted with the first antibody is the same surface to which the apolipoprotein is bound and contacted with the second antibody, that is to say, the contact is performed in a single container, for example, a single well in a plate such as an ELISA plate. Therefore, the contact between the surface to which the apolipoprotein is bound and the first antibody is performed in the same container as the one wherein the contact with a second antibody is performed. In an alternative preferred embodiment, a first surface to which the apolipoprotein is bound is contacted with the first antibody and a second surface to which the apolipoprotein is bound is contacted with the second antibody, wherein said first and second surfaces are different surfaces, as a way of example, different wells in a plate (such as an ELISA plate), different beads (such as luminex beads of turbidimetric beads) or different particles. Therefore, the contact between the surface to which the apolipoprotein is bound and the first antibody is performed in a different container from the container wherein the contact between the surface to which the apolipoprotein is bound and the second antibody is performed, that is to say, separate containers are used. In a more particular embodiment, when separate containers are used, each of said containers comprises a plurality of entities, e.g. two separate sets of beads (such as luminex beads of turbidimetric beads) or two separate set of particles.

In a preferred embodiment of the second method of the invention, the surface used in step (i) is formed by a plurality of entities, and the contacting with the first antibody and with the second antibody in step (ii) is performed in separate containers, each containing part of the plurality of entities forming the surface.

In a third step of the third method of the invention, the allelic dosage of the apolipoprotein isoform is determined by correlating the amount of complex formed in step (ii) with the number of alleles encoding said genetic variant.

In a particular embodiment, determination of the relative amounts of the isoform with respect to the total apolipoprotein content is carried out based on the levels of the first and second complex obtained in step (ii) and wherein the allelic dosage of haplotypes associated with the expression of an apolipoprotein isoform the apolipoprotein isoform is determined from the relative amounts determined in (iii).

In a particular embodiment, the ratio between the signals derived from the detection of the first and second complexes detected in step (ii) is calculated. As a result, the relative amount of an isoform of a particular apolipoprotein with respect to the total content of said apolipoprotein is determined. As the skilled person acknowledges, the ratio may range between 0 (when the particular apolipoprotein isoform is absent in the sample to be analysed), and 1 (when the particular apolipoprotein isoform is the only isoform of said apolipoprotein present in the sample to be analysed). Thus, a ratio equal to zero relates to an absence of the apolipoprotein isoform in the sample analysed. A ratio equal to 1, wherein 1 is an arbitrary value in arbitrary units, relates to a homozygous subject for the apolipoprotein isoform. A ratio equal to 0.5, wherein 0.5 is an arbitrary value in arbitrary units, relates to an heterozygous subject for the apolipoprotein isoform. Methods for detecting the complexes have described previously and incorporated herein.

In a preferred embodiment of the second method of the invention, the surface used in step (i) is formed by a plurality of entities, the contacting with the first antibody and with the second antibody in step (ii) is performed in separate containers, each containing part of the plurality of entities forming the surface, and the detection in step (iii) is carried out separately in each container. This embodiment is particularly preferred when the polystyrene of polycarbonate surfaces are comprised by beads, preferably luminex beads or turbidimetric beads, and detection is performed by means of immunoturbidimetry. Thus, first and second complexes formed in the second step of the method are detected by turbidimetry, particularly by means of an immunoturbidimetric assay. Formation of a complex apolipoprotein (all isoforms thereof)-antibody or a complex apolipoprotein isoform-antibody, when said apolipoprotein or apolipoprotein isoform is present in the sample to be analysed, results in an increase of turbidity compared to turbidity in a sample lacking the apolipoprotein or apolipoprotein isoform, wherein said turbidity variation can be measured (for example, by means of a spectrophotometer). In a preferred embodiment of the invention, the immunoturbidimetric assay is LEIT.

In a particular alternative embodiment, first and second complexes formed in the second step of the method are detected by means of a detectable reagent. Suitable detectable reagents in the context of the invention have been described previously and incorporated herein. In a preferred embodiment, first and second complexes formed in the second step of the method are detected by means of a reporter antibody, which is specific for the anti-apolipoprotein antibody and/or the anti-apolipoprotein isoform antibody. In a preferred embodiment, the second antibody (reporter antibody) is conjugated with an enzyme, in conditions similar to the conditions of incubation of the surface with the apolipoprotein isoform and/or of incubation of the antibody specific for the apolipoprotein isoform with the apolipoprotein isoform bound to the surface. This embodiment is particularly preferred when the polystyrene of polycarbonate surfaces are comprised by a plate, preferably an ELISA plate, and when detection is performed by means of an ELISA assay.

As a result, a ratio equal to zero identifies the absence of an apolipoprotein isoform in the sample analyzed, that is to say, the dosage for a particular allele encoding a genetic variant is zero. A ratio equal to 1 relates to an homozygous subject for the apolipoprotein isoform, that is to say, the dosage of a particular allele encoding a genetic variant is two. A ratio equal to 0.5 relates to an heterozygous subject for the apolipoprotein isoform, that is to say, one dose of a particular allele encoding a genetic variant is present.

In a particular preferred embodiment of the third method of the invention, the surface used in step (i) is formed by a plurality of entities, step (ii) further comprises contacting the surface with a second antibody which is capable of binding to all the isoforms of said apolipoprotein present in the sample, wherein said contacting is carried out under conditions suitable for the formation of a first complex comprising the first antibody and the apolipoprotein isoform and for the formation of a second complex comprising the second antibody and all the isoforms of said apolipoprotein, wherein the contacting with the first and with the second antibody is carried out in separate containers, each containing part of the plurality of entities forming the surface, wherein the determination of the relative amounts of the isoform with respect to the total apolipoprotein content is carried out based on the levels of the first and second complex obtained in step (ii), and the allelic dosage of haplotypes associated with the expression of an apolipoprotein isoform the apolipoprotein isoform is determined from the relative amounts determined in step (iii).

Methods for the Prediction of the Development of Neurodegenerative Disease

The presence of ApoE ε4 gene on chromosome 19 in a subject is known to increase the risk of developing Alzheimer disease (AD) in said subject. Accordingly, it has been determined that the presence of one apoE4 allele in a subject is related to a four-fold increased probability of AD development than a subject who carries no apoE4 alleles, and the presence of two apoE4 alleles in a subject is related to a 15-20-fold increased probability of AD development than a subject who carries no apoE4 alleles. Therefore, the methods of the invention for determining apolipoprotein isoforms, including apoE4, may be applied to AD development prediction in a subject.

Thus, in a further aspect, the invention relates to a method for determining the probability that a subject develops a neurodegenerative disease that comprises determining in a sample from said subject the levels of apoE4 isoform by any of the methods of the invention previously described (first, second and third methods), wherein if the apoE4 levels are above a reference value, then it is indicative that the subject has a high probability of suffering from a neurodegenerative disease.

The reference value according to the method of the invention for determining the probability of development of a neurodegenerative disease is the level of apoE4 as determined in a sample from a subject who carries no apoE4 alleles.

The reference value or reference level according to the methods of the invention can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested. Various considerations are taken into account when determining the reference value of the marker. Among such considerations are the age, weight, sex, general physical condition of the patient and the like. For example, equal amounts of a group of at least 2, at least 10, at least 100 to preferably more than 1000 subjects, preferably classified according to the foregoing considerations, for example according to various age categories, are taken as the reference group.

A high probability of developing a neurodegenerative disease occurs in a situation wherein the subject shows at least 5%, at least 10%, at least 20%, at least 30%, at least 40%, at least 50%, at least 60%, at least 70%, at least 80%, at least 90%, at least 100% probabilities of developing or suffering said disease over time. In a particular embodiment, a high probability is at least 100%. In other embodiments, a high probability is at least 200%, at least 300%, at least 400%, at least 500%, at least 700%, at least 800%, at least 900% and at least 1000%. Other cut-offs or ranges as deemed suitable by the person skilled in the art to characterize the invention are however also contemplated, and those are also within scope of the present invention. According to the predictive method of the invention, a high probability of developing a neurodegenerative disease by a subject is related to the presence of one or two apoE4 alleles in the genome of said subject, wherein said apoE4 alleles determination is performed by any of the first, second or third methods of the invention as previously described.

A low probability of developing a neurodegenerative disease occurs in a situation wherein the subject shows at least 5%, at least 10%, at least 20%, at least 30%, at least 40%, at least 50%, at least 60%, at least 70%, at least 80%, at least 90%, at least 100% probabilities of not developing or suffering said disease over time. In a particular embodiment, a low probability is at least 100%. In other embodiments, a low probability is at least 200%, at least 300%, at least 400%, at least 500%, at least 700%, at least 800%, at least 900% and at least 1000%. Other cut-offs or ranges as deemed suitable by the person skilled in the art to characterize the invention are however also contemplated, and those are also within scope of the present invention. According to the predictive method of the invention, a low probability of developing a neurodegenerative disease by a subject is related to the presence of no apoE4 alleles in the genome of said subject, wherein said apoE4 alleles determination is performed by any of the first, second or third methods of the invention as previously described.

In a particular embodiment, the neurodegenerative disease is selected from the group consisting of Alzheimer's disease (AD), cerebral amyloid angiopathy (CAA), Down's syndrome-associated dementia, vascular dementia, Parkinson disease, dementia with Lewy bodies, and Creutzfeldt-Jakob disease. In a more particular embodiment, the neurodegenerative disease is Alzheimer's disease (AD).

In a further aspect, the invention relates to a method for determining the probability that a subject develops a neurodegenerative disease that comprises determining in said subject the allelic dosage of the haplotype encoding the ApoE4 isoform by the third method of the invention, wherein the presence of one or two ApoE4 alleles in the genome of the subject is indicative that the subject has a high probability of suffering from a neurodegenerative disease, and wherein the presence of no ApoE4 alleles in the genome of the subject is indicative that the subject has a low probability of suffering from a neurodegenerative disease.

In a particular embodiment, the neurodegenerative disease is selected from the group consisting of Alzheimer's disease (AD), cerebral amyloid angiopathy (CAA), Down's syndrome-associated dementia, vascular dementia, Parkinson disease, dementia with Lewy bodies, and Creutzfeldt-Jakob disease. In a preferred embodiment, the neurodegenerative disease is Alzheimer's disease (AD).

Methods for the Prediction of the Development of Cardiovascular Disease

Apolipoprotein deficiencies have been associated to the development of cardiovascular diseases. Therefore, the methods of the invention for determining apolipoproteins and apolipoprotein isoforms may be applied as well to the prediction of cardiovascular disease development risk.

Thus, in another aspect, the present invention relates to a method for determining the probability that a subject develops a cardiovascular disease that comprises determining in a sample from said subject the levels of an apolipoprotein isoform by any of the methods of the invention previously described (first, second and third methods), wherein if the apolipoprotein isoform levels are above a reference value, then it is indicative that the subject has a high probability of suffering from a cardiovascular disease.

In another aspect, the invention relates to a method for determining the probability that a subject develops a cardiovascular disease that comprises determining in said subject the allelic dosage of the haplotype encoding an apolipoprotein isoform by the third method of the invention, wherein the presence of one or two alleles of said apolipoprotein isoform in the genome of the subject is indicative that said subject has a higher probability of suffering from a cardiovascular disease, and wherein the presence of no alleles of said apolipoprotein isoform in the genome of the subject is indicative that said subject has a lower probability of suffering from a cardiovascular disease.

In an embodiment of the cardiovascular disease prediction methods of the invention, the apolipoprotein isoform to be determined is an apoE isoform, particularly selected from the group consisting of apoE isoforms apoE E2, apoE E3 and apoE E4, and the cardiovascular disease is selected from the group consisting of hyperlipoproteinemia type III (also known as dysbetalipoproteinemia or broad beta disease, a rare genetic disorder characterized by improper metabolism of lipids, specifically cholesterol and triglycerides, resulting in the abnormal accumulation of lipids in the body or hyperlipidemia), dysbetalipoproteinemia due to defect in apolipoprotein e-d, familial hyperbetalipoproteinemia (increased accumulation of low density lipoproteins or betalipoproteins in the blood) and prebetalipoproteinemia (excess of very low density lipoproteins or pre-beta lipoproteins in the blood), familial hypercholesterolemia with hyperlipemia, hyperlipemia with familial hypercholesterolemic xanthomatosis (deposition of cholesterol-rich accumulations in the body), broad-betalipoproteinemia (a condition characterized by the development of areas of excess fat in different parts of the body, so that fat is stored in abnormal places throughout the body including the palm, fingers, knees, elbows, and under the arms), floating-betalipoproteinemia and coronary artery disease (hardening and narrowing of the arteries supplying blood to heart muscle, resulting in atherosclerosis, and even angina or heart attack).

In another embodiment of the cardiovascular disease prediction methods of the invention, the apolipoprotein to be determined is apoAI, and the cardiovascular disease is hypoalphalipoproteinemia (a HDL deficiency, inherited in an autosomal dominant manner).

In another embodiment of the cardiovascular disease prediction methods of the invention, the apolipoprotein to be determined is apoCII, and the cardiovascular disease is hyperlipoproteinemia type Ib (a rare inherited condition resulting from low apoCII levels that is characterized by high levels of chylomicrons).

In another embodiment of the cardiovascular disease prediction methods of the invention, the apolipoprotein to be determined is apoCIII, and the cardiovascular disease is apoCIII deficiency associated with hypertriglycidemia (increased blood levels of triglycerides).

Kits of the Invention and Uses Thereof

In a further aspect, the invention relates to a kit comprising a polystyrene or a polycarbonate surface and an antibody specific for an apolipoprotein or isoform thereof, wherein the kit does not comprise a second antibody specific for said apolipoprotein or isoform thereof.

Thus, a first element of the kit of the invention is a polystyrene or a polycarbonate surface. Polystyrene and polycarbonate surfaces according to the invention have been described previously in the context of the first method of the invention and incorporated herein. Preferably, the surface is a polystyrene surface. In a particular embodiment, the polystyrene or polycarbonate surface is comprised by an ELISA plate, luminex beads, turbidimetric beads or a protein array. Particular preferred surfaces are polystyrene surfaces including, without limitation, plates such as ELISA plates, beads such as luminex beads and turbidimetric beads, and particles.

A second element of the kit of the invention is an antibody specific for an apolipoprotein or isoform thereof. Apolipoproteins according to the kit of the invention include apoCI, apoAIV, apoCI, apoCII, apoCIII, apoE and apoJ (clusterin). Apolipoprotein isoforms according to the kit of the invention include apoCI, apoAIV, apoCI, apoCII, apoCIII, apoE and apoJ (clusterin) isoforms. Antibodies specific for an apolipoprotein or isoform thereof have been described previously and incorporated herein. In a particular embodiment, the apolipoprotein is apoE and the antibody an anti-apoE antibody. In a particular embodiment, the apolipoprotein isoforms are apoE isoforms selected from the group consisting of apoE2, apoE3 and apoE4, and the antibodies are selected from the group consisting of anti-apoE2, anti-apoE3 and anti-apoE4 antibodies.

In a particular embodiment, the antibody specific for an apolipoprotein or isoform thereof of the kit of the invention is bound to the polystyrene or the polycarbonate surface, preferably polystyrene surface.

The kit of the invention does not comprise a second antibody specific for the particular apolipoprotein or the particular isoform thereof for which the antibody comprised by the kit is specific for. However, in a particular embodiment, when the antibody comprised by the kit is an antibody specific for a particular apolipoprotein isoform, then the kit may further comprise a second antibody which is capable of binding to all the isoforms of said particular apolipoprotein.

In a particular embodiment, the kit of the invention further comprises a reporter antibody, wherein said reporter antibody is specific for the antibody specific for an apolipoprotein or isoform thereof comprised by said kit. In a particular alternative embodiment, the antibody specific for an apolipoprotein or isoform thereof of the kit of the invention comprises a detectable reagent. Suitable detectable reagent in the context of the present invention have been described previously in the context of the first method of the invention and incorporated herein.

In a further embodiment, the invention relates to the use of the kit as described above for detecting and/or quantifying an apolipoprotein or isoform thereof in a sample, for determining the relative amount of an isoform of a given apolipoprotein with respect to the total content of said apolipoprotein in a sample, for determining the allelic dosage of haplotypes associated with the expression of an apolipoprotein isoform in a subject, for determining the probability that a subject develops a neurodegenerative disease, or for determining the probability that a subject develops a cardiovascular disease. In a particular embodiment, the invention relates to the use of a kit as described above for detecting and/or quantifying an apolipoprotein selected from the group consisting of apoCI, apoAIV, apoCI, apoCII, apoCIII, apoE and apoJ (clusterin) or an isoform thereof. In a more particular embodiment, the invention relates to the use of a kit as described above for detecting and/or quantifying an apolipoprotein selected from the group consisting of apoCI, apoAIV, apoCI, apoCII, apoCIII, apoE and apoJ (clusterin) or an isoform thereof, wherein the polystyrene or polycarbonate surface is blocked with albumin, even more preferably wherein the albumin is BSA. Particular details of these determinations have been described along the present description and are incorporated herein.

Accordingly, the present invention relates to the following aspects:

1. An in vitro method for the detection and/or quantification of an apolipoprotein or an isoform thereof in a sample that comprises:
(i) Contacting the sample with a polystyrene or a polycarbonate surface under suitable conditions for the binding of the apolipoprotein or the isoform thereof to the surface, wherein the surface contains no antibodies specific for said apolipoprotein or isoform thereof bound to it,
(ii) Contacting the surface to which the apolipoprotein or the isoform thereof is bound formed in step (i) with an antibody specific for said apolipoprotein or for said isoform thereof under suitable conditions for the formation of a complex between the antibody and the apolipoprotein or the isoform thereof, and
(iii) Detecting the complexes formed in step (ii).
2. The method according to aspect 1 wherein the apolipoprotein is selected from the group consisting of apoAI, apoAIV, apoCI, apoCII, apoCIII, apoE and apoJ (clusterin).
3. An in vitro method for determining the relative amount of an isoform of a given apolipoprotein with respect to the total content of said apolipoprotein in a sample that comprises:
(i) Contacting the sample with a polystyrene or a polycarbonate surface under suitable conditions for the binding of the apolipoprotein to the surface, wherein the surface contains no antibodies specific for said apolipoprotein bound to it,
(ii) Contacting the surface to which the apolipoprotein is bound formed in step (i) with a first antibody specific for said apolipoprotein isoform and with a second antibody which is capable of binding to all the isoforms of said apolipoprotein present in the sample, wherein said contacting is carried out under conditions suitable for the formation of a first complex comprising the first antibody and the apolipoprotein isoform and for the formation of a second complex comprising the second antibody and all the isoforms of said apolipoprotein,
(iii) Detecting the first and second complexes formed in step (ii) and
(iv) Determining the relative amounts of the isoform with respect to the total apolipoprotein content based on the levels of the first and second complex obtained in step (iii).
4. The method of aspect 3 wherein the surface used in step (i) is formed by a plurality of entities, wherein the contacting in step (ii) with the first antibody and with the second antibody is performed in separate containers, each container containing part of the plurality of entities forming the surface, and wherein the detection in step (iii) is carried out separately in each container.
5. The method according to aspects 3 or 4 wherein the apolipoprotein isoform is an isoform of an apolipoprotein selected from the group consisting of apoAI, apoAIV, apoCI, apoCII, apoCIII, apoE and apoJ (clusterin).
6. The method according to aspect 5, wherein the apolipoprotein is apoE and the apoE isoform is selected from the group consisting of apoE2, apoE3 and apoE4.
7. A method for determining the allelic dosage of haplotypes associated with the expression of an apolipoprotein isoform in a subject comprising,
(i) Contacting a protein-containing sample from said subject derived from a tissue wherein the apolipoprotein isoform is expressed with a polystyrene or polycarbonate surface under suitable conditions for the binding of the apolipoprotein isoform to the surface, wherein the surface contains no antibodies specific for said apolipoprotein isoform bound to it,
(ii) Contacting the surface to which the apolipoprotein is bound formed in step (i) with at least one antibody specific for the apolipoprotein isoform under suitable conditions for the formation of a complex between the antibody and the apolipoprotein isoform,
(iii) Determining the allelic dosage of the apolipoprotein isoform by correlating the amount of complex formed in step (ii) with the number of alleles encoding said genetic variant.
8. The method of aspect 7, wherein the surface used in step (i) is formed by a plurality of entities, wherein step (ii) further comprises contacting the surface with a second antibody which is capable of binding to all the isoforms of said apolipoprotein present in the sample, wherein said contacting is carried out under conditions suitable for the formation of a first complex comprising the first antibody and the apolipoprotein isoform and for the formation of a second complex comprising the second antibody and all the isoforms of said apolipoprotein, wherein the contacting with the first and with the second antibody is carried out in separate containers, each containing part of the plurality of entities forming the surface, wherein the determination of the relative amounts of the isoform with respect to the total apolipoprotein content is carried out based on the levels of the first and second complex obtained in step (ii) and wherein the allelic dosage of haplotypes associated with the expression of an apolipoprotein isoform the apolipoprotein isoform is determined from the relative amounts determined in step (iii).
9. The method according to aspects 7 or 8 wherein the genetic variant encoding the apolipoprotein isoform is a gene encoding an isoform of an apolipoprotein selected from the group consisting of apoAI, apoAIV, apoCI, apoCII, apoCIII, apoE and apoJ (clusterin).
10. The method according to aspect 9, wherein the gene encoding the apolipoprotein isoform is the gene encoding apoE4.
11. The method according to any of the preceding aspects, wherein the sample is selected from the group consisting of blood, plasma, serum, saliva, urine and cerebrospinal fluid (CSF).
12. The method according to the preceding aspect wherein the sample is plasma, preferably in a dilution ranging from 1:10 to 1:100000, preferably from 1:100 to 1:1000, more preferably 1:200.
13. The method according to any of the preceding aspects, wherein the polystyrene or polycarbonate surface is blocked prior to the binding step (i).
14. The method according to the preceding aspect, wherein the surface is blocked by a protein other than an apolipoprotein and/or by a detergent.
15. The method according to the preceding aspect, wherein the surface is blocked by means of a protein selected from the group consisting of BSA, casein, and gelatin, and wherein the detergent is selected from the group consisting of polyvinylpyrolidone-40 (PVP-40), polysorbate20, Nonidet-P40, and Triton X-100.

16. The method according to the preceding aspect, wherein the surface is blocked by BSA, preferably BSA 1%.
17. The method according to any of the preceding aspects wherein the polystyrene surface is treated with a washing solution after the binding step (i).
18. The method according to the preceding aspect wherein the washing solution contains one or more salts.
19. The method according to the preceding aspect wherein the salt is NaCl.
20. The method according to any of aspects 17 to 19 wherein the washing solution contains at least one detergent.
21. The method according to the preceding aspect wherein the at least one detergent is selected from the group consisting of polysorbate 20 and Triton X-100.
22. The method according to aspect 17 to 21 wherein the washing solution contains an acid.
23. The method according to the preceding aspect wherein the acid is 2M HCl or formic acid 70%.
24. The method according to any of aspects 17 to 21 wherein the washing solution contains a base.
25. The method according to the preceding aspect wherein the base is 2M NaOH.
26. The method according to any of aspects 17 to 25 wherein the washing solution contains a reducing agent.
27. The method according to the preceding aspect wherein the reducing agent is 2-mercaptotethanol.
28. The method according to any of aspects 17 to 27 wherein the washing solution does not contain a protease, an oxidizing reagent or the combination thereof.
29. The method according to any of the preceding aspects, wherein the polystyrene or polycarbonate surface is comprised by an ELISA plate, luminex beads or turbidimetric beads.
30. The method according to any of the preceding aspects, wherein complex detection in step (iii) is performed by ELISA, or by an immunoturbidimetric assay.
31. The method according to the preceding aspect, wherein the immunoturbidimetric assay is a LEIT (Latex-Enhanced Immunoturbidimetry Technology).
32. The method according to any of aspects 1-30, wherein the detection of the complexes formed in step (iii) is performed by means of a reporter antibody specific for the anti-apolipoprotein antibody.
33. A method for determining the probability that a subject develops a neurodegenerative disease that comprises determining in a sample from said subject the levels of apoE4 isoform by a method according to any of aspects 1 to 32, wherein if the apoE4 levels are above a reference value, then it is indicative that the subject has a high probability of suffering from a neurodegenerative disease.
34. A method for determining the probability that a subject develops a neurodegenerative disease that comprises determining in said subject the allelic dosage of the haplotype encoding the apoE E4 isoform by a method according to any of aspects 7 to 32, wherein the presence of one or two apoE E4 alleles in the genome of the subject is indicative that the subject has a high probability of suffering from a neurodegenerative disease, and wherein the presence of no apoE4 alleles in the genome of the subject is indicative that the subject has a low probability of suffering from a neurodegenerative disease.
35. The method according to any of aspects 33 or 34 wherein the neurodegenerative disease is selected from the group consisting of Alzheimer's disease (AD), cerebral amyloid angiopathy (CAA), Down's syndrome-associated dementia, vascular dementia, Parkinson disease, dementia with Lewy bodies, and Creutzfeldt-Jakob disease.
36. The method according to the preceding aspect, wherein the neurodegenerative disease is Alzheimer's disease (AD).
37. A method for determining the probability that a subject develops a cardiovascular disease that comprises determining in a sample from said subject the levels of an apolipoprotein isoform by a method according to any of aspects 1 to 30, wherein if said apolipoprotein isoform levels are above a reference value, then it is indicative that the subject has a high probability of suffering from a cardiovascular disease.
38. A method for determining the probability that a subject develops a cardiovascular disease that comprises determining in said subject the allelic dosage of the haplotype encoding an apolipoprotein isoform by a method according to any of aspects 7 to 30, wherein the presence of one or two alleles of said apolipoprotein isoform in the genome of the subject is indicative that said subject has a higher probability of suffering from a cardiovascular disease, and wherein the presence of no alleles of said apolipoprotein isoform in the genome of the subject is indicative that said subject has a lower probability of suffering from a cardiovascular disease.
39. The method according to aspects 37 or 38, wherein the apolipoprotein isoform is an apoE isoform and the cardiovascular disease is selected from the group consisting of hyperlipoproteinemia type III, dysbetalipoproteinemia due to defect in apolipoprotein e-d, familial hyperbeta- and prebetalipoproteinemia, familial hypercholesterolemia with hyperlipemia, hyperlipemia with familial hypercholesterolemic xanthomatosis, broad-betalipoproteinemia, floating-betalipoproteinemia and coronary artery disease.
40. The method according to aspects 37 or 38, wherein the apolipoprotein isoform is apoCI and the cardiovascular disease is hypoalphalipoproteinemia.
41. The method according to aspects 37 or 38, wherein the apolipoprotein isoform is apoCII and the cardiovascular disease is hyperlipoproteinemia type Ib.
42. The method according to aspects 37 or 38, wherein the apolipoprotein isoform is apoCIII and the cardiovascular disease is apoCIII deficiency associated with hypertriglycidemia.
43. A kit comprising a polystyrene or a polycarbonate surface and an antibody specific for an apolipoprotein or isoform thereof, wherein the kit does not comprise a second antibody specific for said apolipoprotein or isoform thereof.
44. The kit according to aspect 43, wherein if the antibody present in the kit is specific for an apolipoprotein isoform, the kit further comprises a second antibody which is capable of binding to all the isoforms of said apolipoprotein.
45. The kit according to aspects 43 or 44 wherein the apolipoprotein is selected from the group consisting of apoCI, apoAIV, apoCI, apoCII, apoCIII, apoE and apoJ (clusterin), and wherein the apolipoprotein isoform is an isoform of an apolipoprotein selected from the group consisting of apoCI, apoAIV, apoCI, apoCII, apoCIII, apoE and apoJ (clusterin).

46. The kit according to aspect 45, wherein the apolipoprotein is apoE and the apoE isoform is selected from the group consisting of apoE2, apoE3 and apoE4.
47. The kit according to any of aspects 43 to 46 wherein the polystyrene or polycarbonate surface is comprised by an ELISA plate, luminex beads or turbidimetric beads.
48. The kit according to any of aspects 43 to 47 further comprising a reporter antibody, wherein said reporter antibody is specific for the antibody specific for an apolipoprotein or isoform thereof of the kit.
49. The kit according to any of aspects 43 to 47, wherein the antibody specific for an apolipoprotein or isoform thereof comprises a detectable reagent.
50. Use of a kit according to any of aspects 43 to 49 for detecting and/or quantifying an apolipoprotein or isoform thereof in a sample, for determining the relative amount of an isoform of a given apolipoprotein with respect to the total content of said apolipoprotein in a sample, for determining the allelic dosage of haplotypes associated with the expression of an apolipoprotein isoform in a subject, for determining the probability that a subject develops a neurodegenerative disease, or for determining the probability that a subject develops a cardiovascular disease.

The invention is described in detail below by means of the following examples, which are to be construed as merely illustrative and not limitative of the scope of the invention.

EXAMPLES

Example 1. ApoE4 Detection by ELISA

Materials and Equipment

- ELISA plates high-binding (Nunc MaxiSorp® flat-bottom 96 well plate. Alternative ELISA plate types and brands can be used with similar results.
- Superblock in TBS (Thermo-Fisher, #PI-37535). Alternative blocking reagents have been used, including gelatin, BSA, casein, Tween-20, among other, with similar results.
- Mouse monoclonal antibody specific for apoE E4, clone 4E4 (Novus Biologicals, #NBP1-49529).

Alternative antibodies specific for apoE E4 have been used (Mouse monoclonal antibody specific for apoE E4, clone 5B5 (IBL #10025); Mouse monoclonal antibody specific for apoE E4, clone 1F9 (MBL, #M067-3)).

- Rabbit polyclonal antibody for total apoE (SantaCruz Biotechnology, Inc., #sc-98573)
- Polysorbate-20 (Tween-20) from Sigma-Aldrich
- Polyclonal antibody anti-mouse IgG peroxidase conjugated.
- TMB Peroxidase EIA Substrate (Biorad)
- ELISA Wash Station (TECAN)
- ELISA spectrophotometer (TECAN)

Detection Method

- Block ELISA plates by adding 200 μl of Superblock (SB) in Tris-buffered saline (TBS) for 16 h at room temperature (RT)
- Wash 2 times with 300 μl of TBS 0.1% Tween20 in ELISA Wash Station.
- Incubate 100 μl of diluted plasma 1:200 in TBS+20% SB for 1 hour at RT.
- Wash 4 times with 300 μl of TBS 0.1% Tween20 in ELISA Wash Station.
- Incubate with 50 μl of reporter antibody: 4E4 antibody diluted 1:2,000 in TBS+20% SB for 45 min at RT.
- Wash 4 times with 300 μl of TBS 0.1% Tween20 in ELISA Wash Station.
- Incubate with 50 μl anti-mouse IgG-peroxidase (1:10,000) in TBS+20% SB for 30 min.
- Wash 4 times with 300 μl of TBS 0.1% Tween20 in ELISA Wash Station.
- Develop by adding 100 μl de TMB for 10 minutes in dark conditions.
- Stop by adding 100 μl of H2SO4 2.15 N.
- Read plate in spectrophotometer at 450 nm with reference at 750 nm.

Different dilutions of the plasma samples have been analyzed, ranging from 1:20 to >1:80000. The best discriminative results are obtained in the range between 1:100 and 1:1,000. For the assays shown herewith, the plasma dilution used is 1:200, unless otherwise stated.

Alternatively, other monoclonal antibodies specific for apoE E4 such as 5B5 and 1F9 were used, but the best results were obtained with 4E4 clone.

Incubation times can be shortened without important variations in the results.

Different biological fluids can be analyzed by the protocol described herewith, but the optimal dilution of the sample has to be determined according to the starting apoE concentration.

Results

Discrimination of the Absence/Presence of apoE E4 in Plasma Samples

The presence/absence of ApoE4 was detected using the protocol described above by using polystyrene plates and a monoclonal antibody specific for the E4 isoform. 230 plasma samples from individuals previously genotyped by real-time PCR (e2/e3, n=16; e2/e4, n=4; e3/e3, n=141; e3/e4, n=59; e4/e4, n=10) were analysed. Validation of the assay (73 ApoE4 carriers, 157 non-ApoE4 carriers) revealed 100% concordance with ApoE genotyping by real-time PCR (see FIG. 1 and Table 1).

TABLE 1

Genotype distribution and ELISA readings of 230 plasma samples analyzed for apoE4 isotyping

| ApoE genotype | n | Mean | Std Dev. | Minimum | Maximum |
|---|---|---|---|---|---|
| 2/3 | 16 | 0.0010 | 0.0025 | −0.001 | 0.008 |
| 3/3 | 141 | 0.0020 | 0.0045 | −0.004 | 0.036 |
| 2/4 | 4 | 3.087 | 0.2189 | 2.713 | 3.097 |
| 3/4 | 59 | 3.093 | 0.3787 | 1.322 | 3.471 |
| 4/4 | 10 | 3.226 | 0.2124 | 2.788 | 3.557 |

Figure 2:
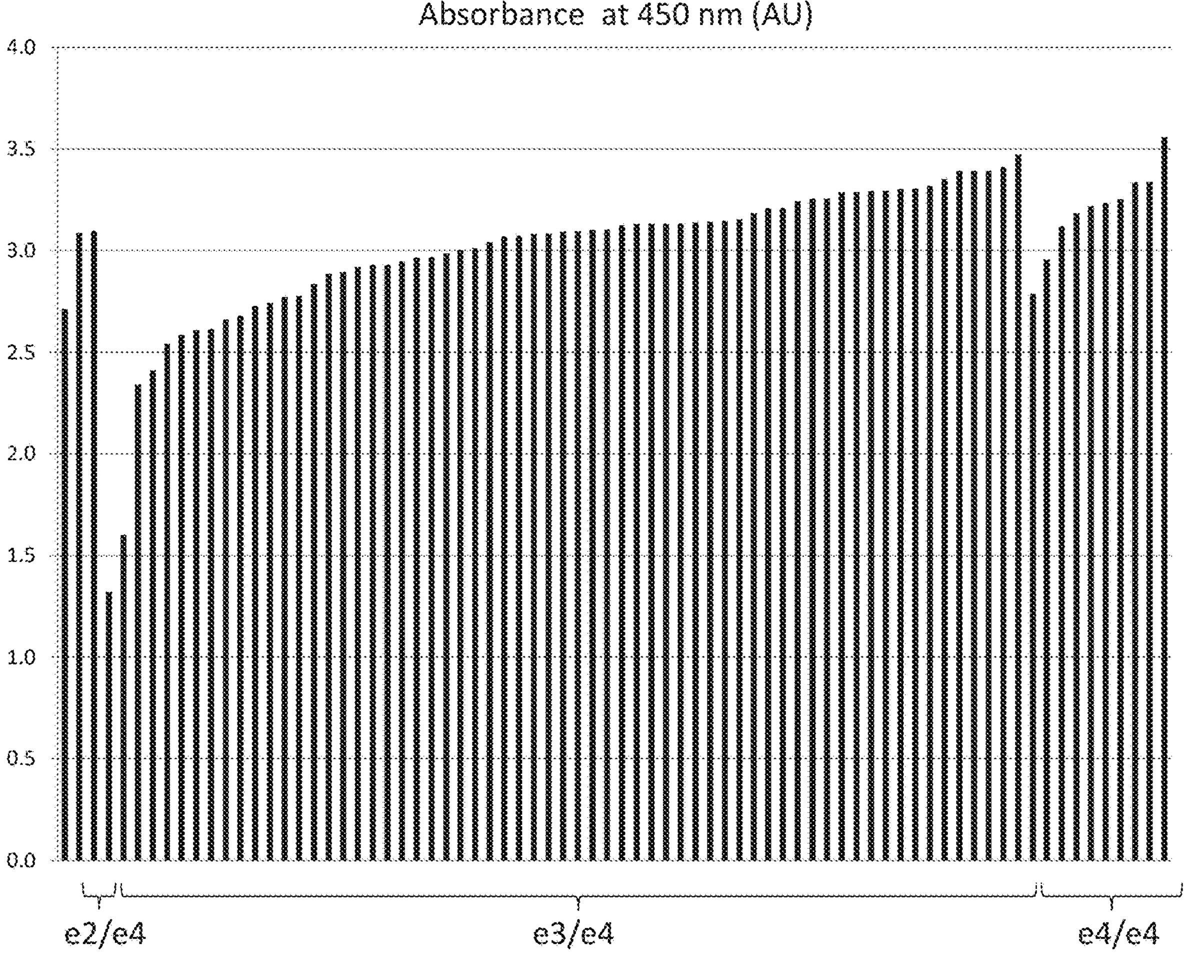
FIG. 2 shows the absorbance ELISA readings of 73 samples containing apoE E4 (from FIG. 1) distributed according to their genotype.
Figure 3:
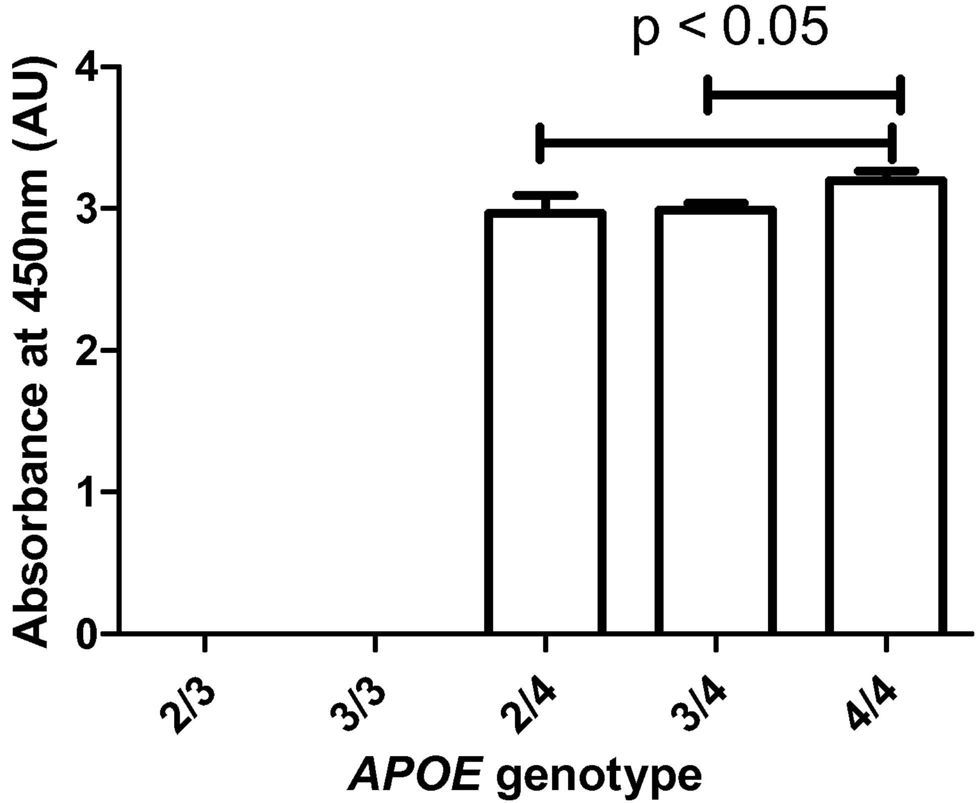
FIG. 3 shows the mean absorbance readings of the 230 samples analyzed, distributed according to APOE genotype. Error bars represent the standard error of the mean.

According to the results shown in Table 1 and FIG. 2, plasma samples from homozygous APOE e4/4 tend to have higher absorbance readings than APOE e3/e4 and e2/e4 heterozygous, suggesting that is possible to differentiate e4 homozygous from heterozygous (see FIG. 3), although there is certain overlapping between groups.

Figure 4:
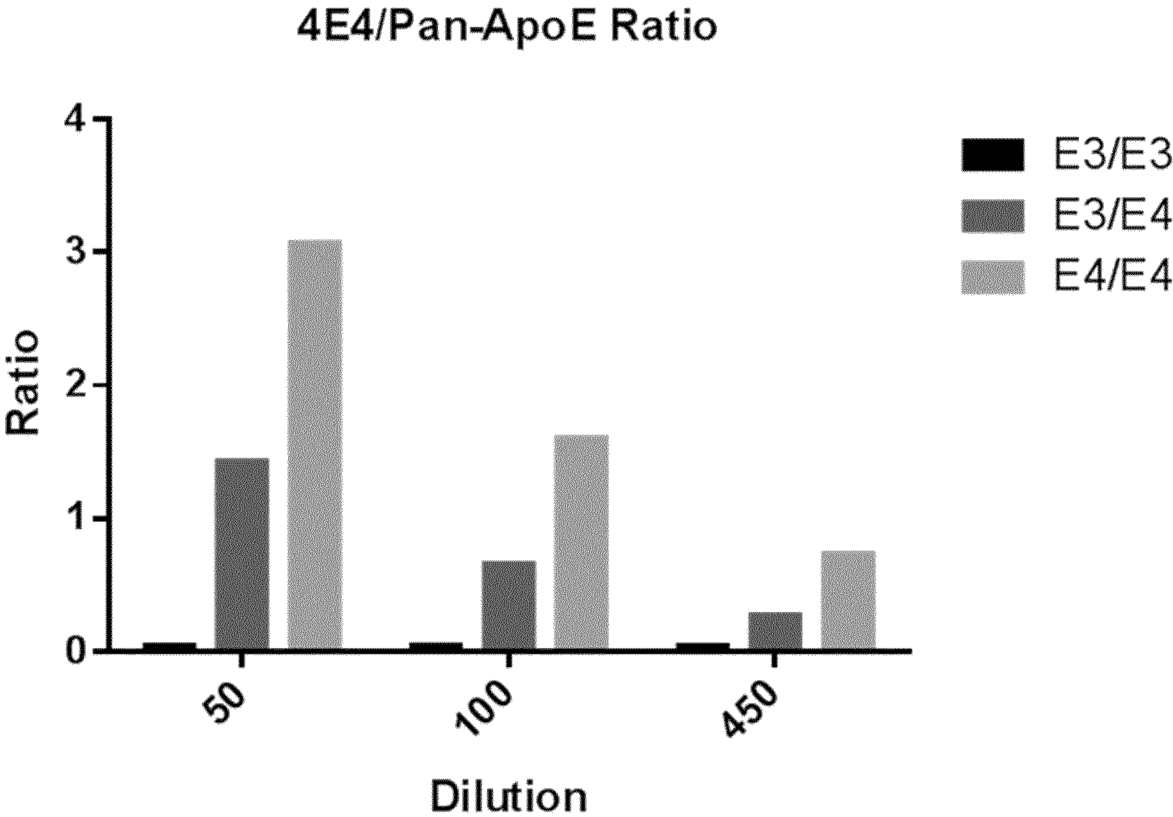
FIG. 4 shows the ratio of apoE E4/total apoE absorbances (4E4/pan-apoE) at different plasma dilutions in APOE e4 non-carriers (E3/E3), and heterozygous (E3/E4) and homozygous (E4/E4) APOE e4 carriers.

Discrimination of the Heterozygous/Homozygous APOE e4 Carriers in Plasma Samples Alternatively, further discrimination between heterozygous and homozygous samples can be accomplished by performing a double ELISA assay for each sample, one specific for apoE E4 and the other to determine the levels of total apoE (reporter antibody: pan-apoE antibody, e.g. polyclonal-pan-apo, SantaCruz Biotech., H-223, #sc-98573). As shown in FIG. 4, the ratio apoE E4/total apoE is a good proxy of the APOE ε4 allele dosage. The discriminative power is good for the three dilutions studied (FIG. 4).

Binding of Different Apolipoproteins to the Polystyrene Surface

Figure 5:
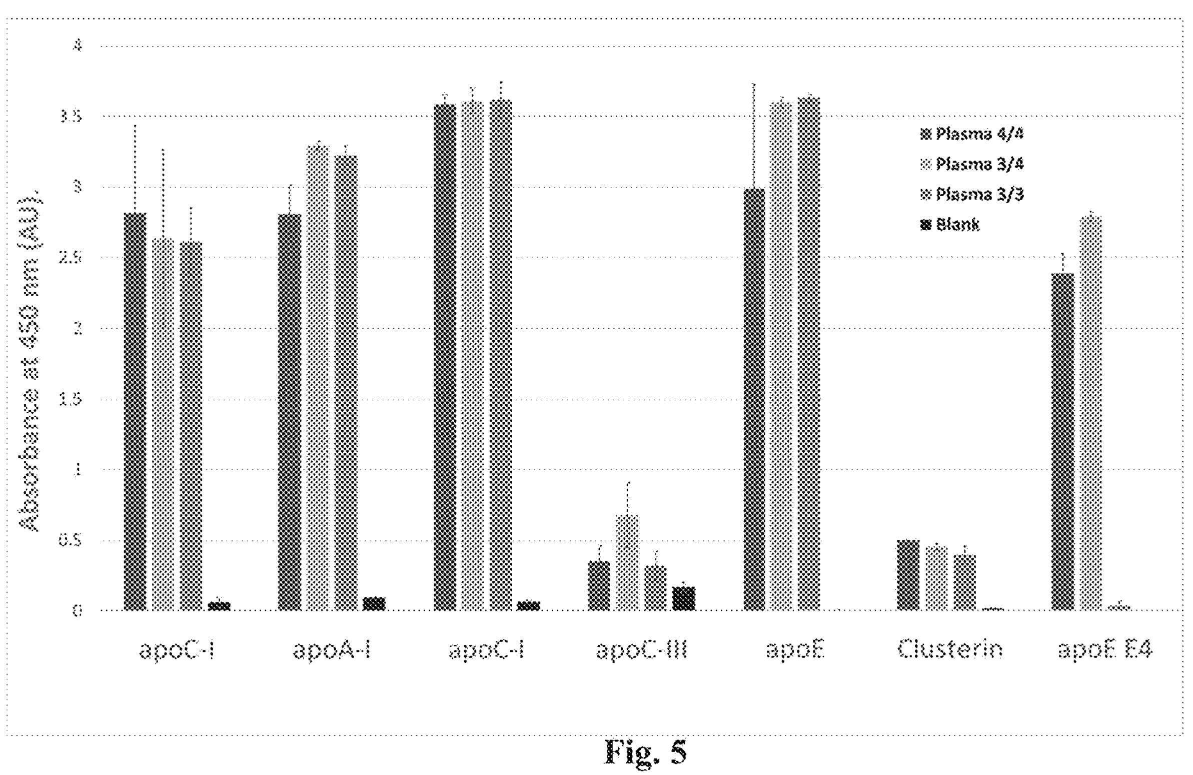
FIG. 5 shows the binding of apolipoproteins from plasma samples (1:200) to a polystyrene surface on an ELISA plate format.

In order to explore the binding of other apolipoproteins to the polystyrene surface, an ELISA protocol as described above was performed, wherein different reporter antibodies specific for certain apolipoproteins were used. The analysis of the results indicated that apoCI, apoAI, apoCIII, total apoE, and clusterin are able to bind to the plate in a similar fashion to apoE E4 (see FIG. 5).

Stable Binding of apoE to the Polystyrene Surface

Figure 6:
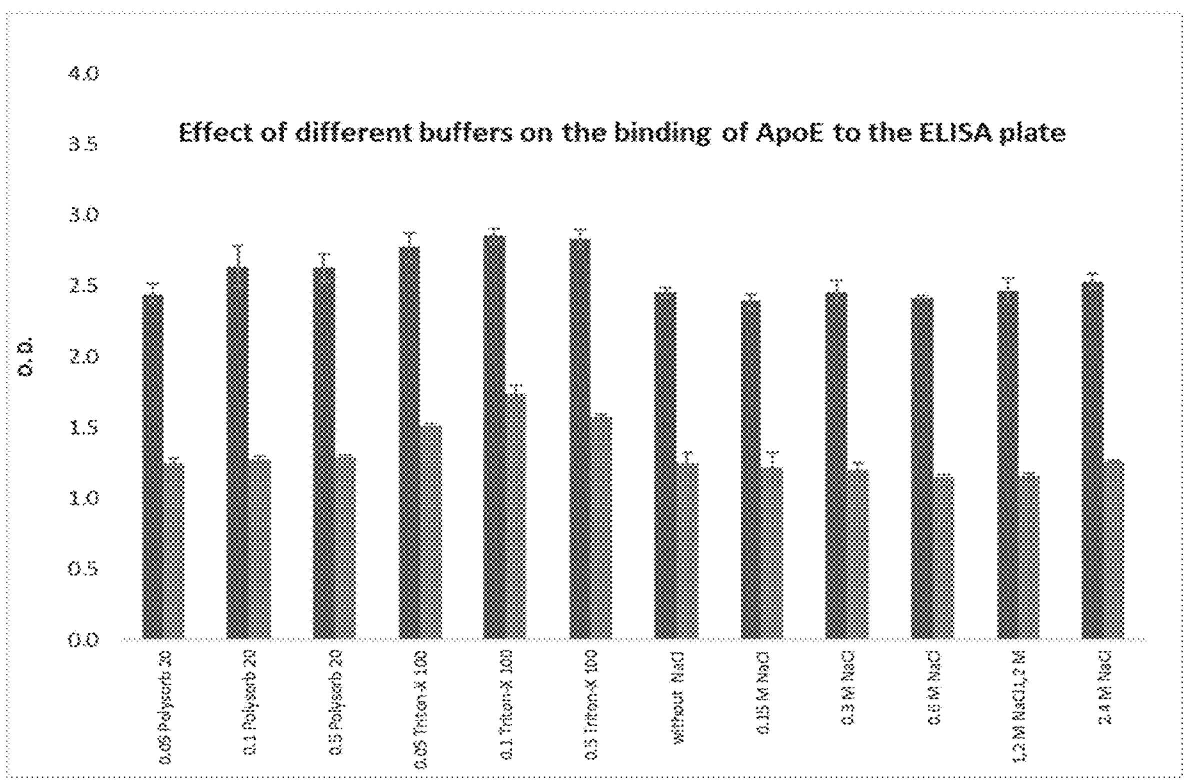
FIG. 6 shows the effect of different buffers containing salt (NaCl 0-2.4 M) or detergent (polysorbate 20-Tween 20- or Triton X-100 from 0-0.5%) on the binding of ApoE to the ELISA plate. Dark and light gray bars represent samples analyzed in wells blocked with a BSA-based or Superblock blocking solutions, respectively.

In order to further characterize the nature of the apoE-polystyrene binding, the ability of different buffers containing salt (NaCl 0-2.4 M) or detergent (polysorbate 20 or Triton X-100 from 0-0.5%) to remove the apoE bound to the polystyrene plate was analyzed. For this purpose, after binding of the apoE present in plasma (1:200 dilution), the wells were incubated for 1 hour at RT with the different buffers of interest, washed and the assay continued as previously described above. As shown in FIG. 6 the presence of increasing concentration of either NaCl or detergents enhances the detection of apoE compared to the control without salt or detergent. These results suggest that the binding is mediated by a combination of both electrostatic and hydrophobic forces (FIG. 6).

Figure 7:
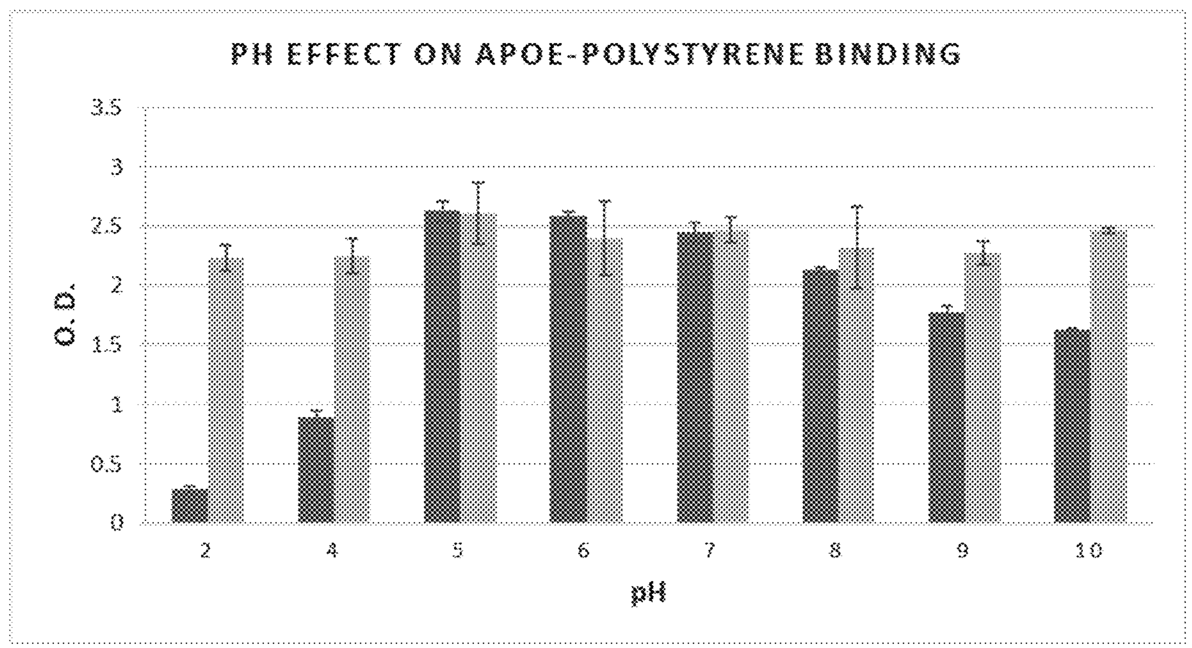
FIG. 7 shows the effect of pH (2-10) on the binding of ApoE to the ELISA plate. Light and dark gray bars represent samples analyzed in wells blocked with a BSA-based or Superblock blocking solutions, respectively.

The stability of the binding apoE-polystyrene was also analyzed as a function of the pH in the range from pH 2 to 10 in wells blocked with either a BSA-based blocking solution or Superblock (FIG. 7). The binding of apoE to the BSA-blocked polystyrene wells was fairly unaffected by the pH in the range studied. Interestingly, the binding of apoE to the Superblock-blocked polystyrene wells was instable at pH below 5 (FIG. 7), suggesting that the presence of BSA may help to maintain a more stable microenvironment because its own buffer capacity. Therefore, further stability analysis were performed on wells blocked with a BSA solution.

More stringent conditions were also assayed (see FIG. 8) by treatment at 56° C. for 1 hour with:

strong acids (2 M HCl or 70% formic acid), strong bases (2 M NaOH), a combination of anionic detergent and a reducing agent (2% SDS and 0.7% 2-mercaptoethanol, "stripping buffer"), sodium hypochlorite (20,000 ppm), and an enzymatic detergent (Coulter Clenz® cleaning agent, Beckman Coulter)

Figure 8:
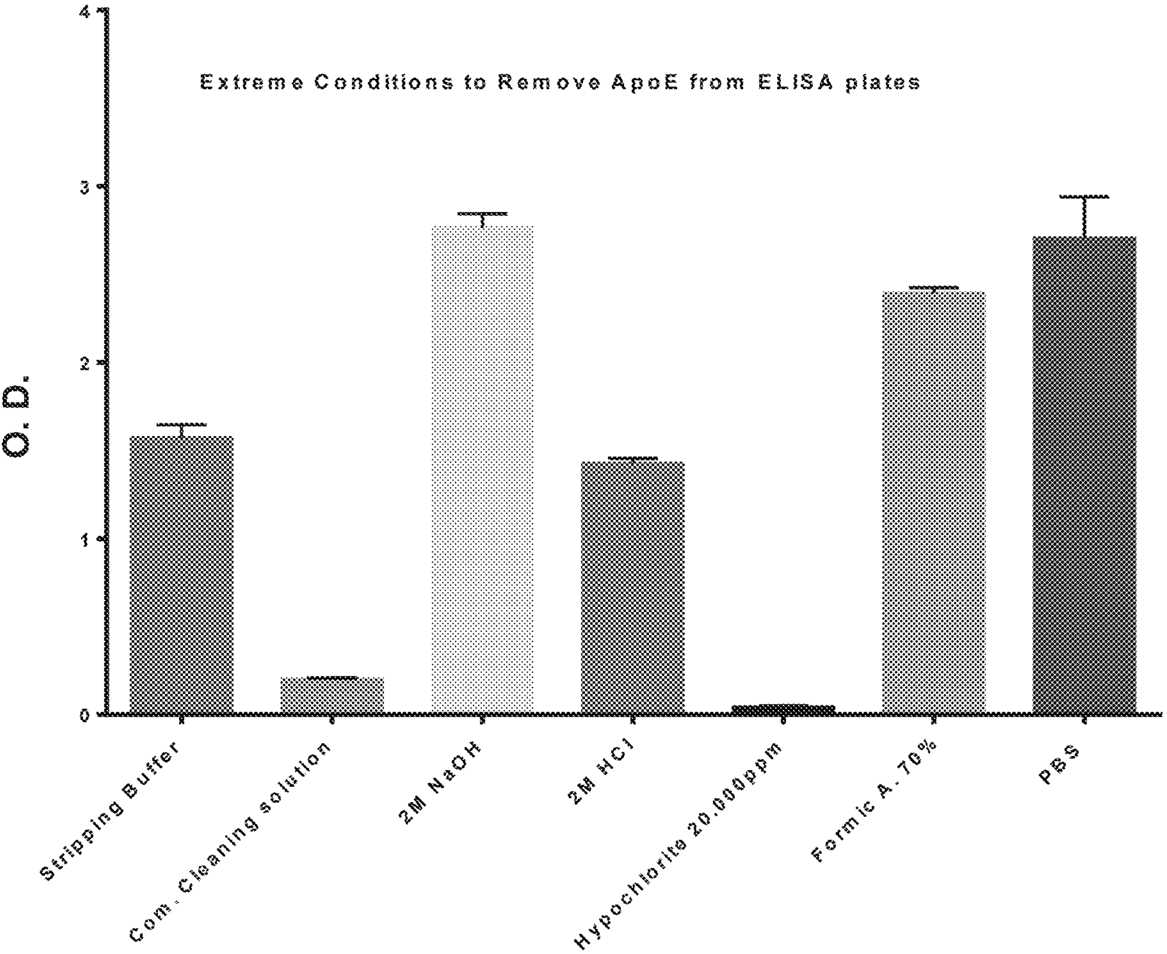
FIG. 8 shows the effect of stringent conditions on the binding of ApoE to the ELISA plate.

Interestingly, the only reagents that were able to remove completely the apoE bound to the plate are those that destroy the protein either by digestion (enzymatic detergent) or by oxidation (sodium hypochlorite) (FIG. 8).

These results indicate that the apoE-polystyrene binding interaction is highly stable, being resistant to strong detergents, acid and basic washes. These properties may allow undertaking immunoassays, protein-microarrays analysis, turbidimetric assays, etc. under highly stringent and specific conditions, precluding the need of additional purification, fractionation or concentration procedures.

Similar results have been observed for the binding of other apolipoproteins to polystyrene; and therefore, similar conclusions are translated to other procedures for different apolipoproteins.

Example 2. ApoE4 Detection by a Turbidimetric Assay

Materials and Equipment

Plasma samples: 11 APOE e3/e3 and 6 APOE e4/e4 samples.

LEIT White microspheres —NH2 coated with Superblock, Prot. 20141222143CM, #143CM1

Spectrophotometer, Ref. UV-3100PC (VWR), Code: PDX-1004

Finnpipette F1 2-20 μL, Ref. 4641060 (Thermoscientific, VWR), Code: PDX-1009

Finnpipette F1 20-200 μL, Ref. 4641080 (Thermoscientific, VWR), Code: PDX-1010

MILI-Q ReferenceA+, Ref. Z00QSVC01

Combi fridge Liebherr, Ref. CN4056, Code: PDM-1000

Vortex Mixer, Ref. VX200 (Labnet, Era biotech), Code: PDX-1013

Optima heated circulating bath, Ref. TC120-ST12 (Grant, VWR), code: PDX-1028

Turbidimetric assays based on Latex-Enhanced Immunoturbidimetry Technology (LEIT) rely on the use of polystyrene beads. Therefore, the inventors used this technology for the analysis apoE E4 and other apolipoproteins exploiting their highly-stable high-affinity interaction with the polystyrene as shown for the ELISA plates.

LEIT is less sensitive than ELISA, but interestingly offers great advantages for relatively high concentrated analytes such as apolipoproteins. LEIT allows running tests in 5-20 minutes and in a fully-automated random access common Clinical Chemistry analyzer. The higher cost in raw material used by LEIT vs ELISA is fully compensated by time saving, easiness and usability of the technology in the clinical laboratories. Then, LEIT is considered as a useful technique for apoE determination.

Figure 9:
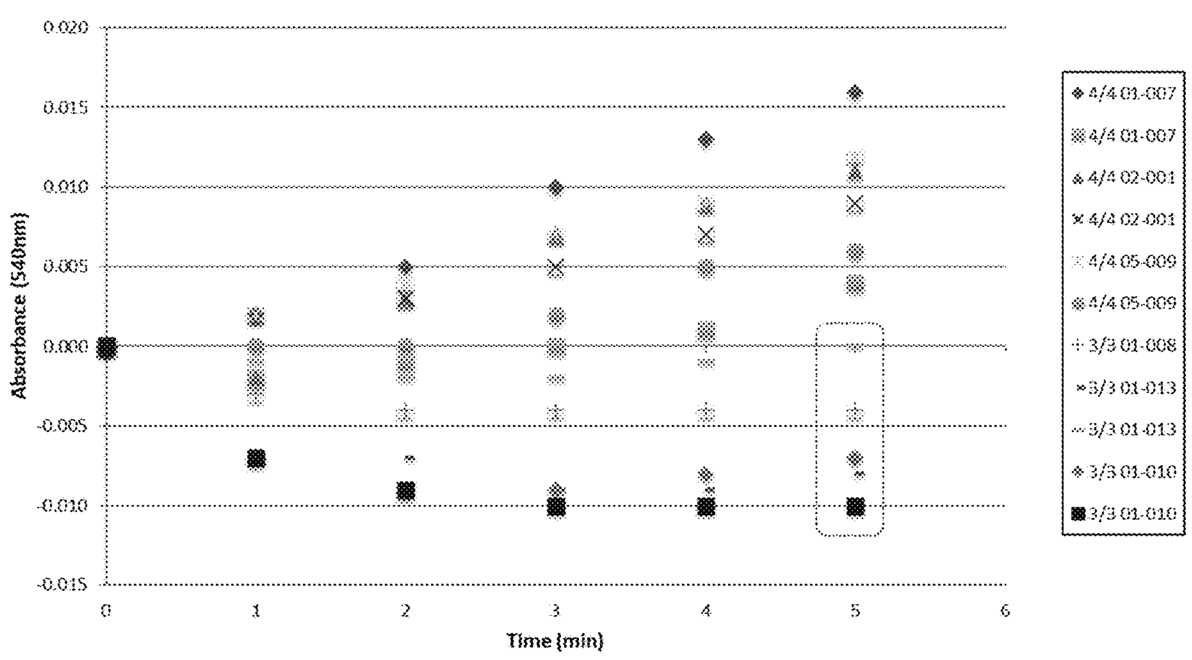
FIG. 9 shows a preliminary analysis of apoE e3/e3 and apoE e4/e4 samples by LEIT at different times.

Preliminary analysis of APOE e3/e3 and 6 APOE e4/e4 plasma samples using the LEIT technology and the monoclonal 4E4 indicated that the procedure is able to differentiate APOE e4 carriers from non-carriers (FIG. 9).

Detection Method (Test 1)

Working Solutions Preparation:

0.5 mL of monoclonal Antibody anti-apoE 4 0.176 mg/mL solution in PBS 10 mM pH 7.3.

Dissolve 88 μL of monoclonal antibody into 4124.

Protocol:

1. Transfer 14.6 μl of LEIT white microspheres —NH2 into an Eppendorf tube and add 131.44 PBS with Tween20 0.01%. Homogenize with micropipette and incubate at 37° C. for 2 min.

2. Add 3.85 μl of apoE sample solution into the same Eppendorf tube, homogenize with micropipette and incubate again for 2 min at 37° C.

3. Add 50 μL of monoclonal antibody solution, homogenize with micropipette and transfer the whole volume into a quartz cuvette.

4. Read absorbance for a minimum time of 5 minutes and a maximum time of 10 minutes.

Detection Method (Test 2)

Working Solutions Preparation:

0.5 mL of monoclonal Antibody anti-apoE 4 0.044 mg/mL solution in PBS 10 mM pH 7.3.

Dissolve 22 μL of monoclonal antibody into 478 μL.

Protocol:

1. Transfer 14.6 μL of LEIT white microspheres —NH2 into an Eppendorf tube and add 131.4 μL PBS with Tween20 0.01% (#144CM1). Homogenize with micropipette and incubate at 37° C. for 2 min.

2. Add 3.85 μl of apoE sample solution into the same Eppendorf tube, homogenize with micropipette and incubate again for 2 min at 37° C.

3. Add 50 μL of monoclonal antibody solution, homogenize with micropipette and transfer the whole volume into a quartz cuvette.

4. Read absorbance for a minimum time of 5 minutes and a maximum time of 10 minutes.

Results

Test 1

Results of tests 1 and 2 for apoE analysis by LEIT at different times are shown in Tables 2 and 3, respectively.

TABLE 2

Analysis of 3 e4/e4, 3 e3/e4, and 3 e3/e3 samples by LEIT at different times by test 1

| | Absorbance (a.u., λ = 540 nm) genotype ID code | | | | | | |
|---|---|---|---|---|---|---|---|
| | 4/4 | | | | 3/4 | | |
| | 01-007 | | | | | | |
| t (min) | MAb | NO MAb | 05-009 MAb | 02-001 MAb | 01-003 MAb | 01-006 MAb | 01-016 MAb |
| 0 | 0.935 | 0.921 | 0.954 | 0.960 | 0.907 | 0.916 | 0.887 |
| 1 | 0.941 | 0.917 | 0.956 | 0.963 | 0.905 | 0.916 | 0.886 |
| 2 | 0.952 | 0.916 | 0.963 | 0.970 | 0.904 | 0.918 | 0.888 |
| 3 | 0.963 | 0.915 | 0.972 | 0.980 | 0.905 | 0.921 | 0.892 |
| 4 | 0.971 | 0.915 | 0.983 | 0.990 | 0.905 | 0.924 | 0.897 |
| 5 | 0.978 | 0.915 | 0.992 | 0.999 | 0.905 | 0.927 | 0.902 |
| $\Delta mAbs_{0-5}$ | 0.043 | −0.006 | 0.038 | 0.039 | −0.002 | 0.011 | 0.015 |

| | Absorbance (a.u., λ = 540 nm) Genotype ID code | | | | | | |
|---|---|---|---|---|---|---|---|
| | | | | | CONTROLS | | |
| | 3/3 | | | | | | 4/4 01-007 |
| | 01-010 | | 01-008 | 01-013 | NO apoE | Goat serum | αM |
| t (min) | MAb | no MAb | MAb | MAb | MAb | MAb | 0.176 mg/ml |
| 0 | 0.970 | 0.903 | 0.924 | 0.932 | 0.888 | 0.884 | 0.882 |
| 1 | 0.967 | 0.900 | 0.920 | 0.929 | 0.887 | 0.881 | 0.878 |
| 2 | 0.966 | 0.899 | 0.918 | 0.928 | 0.888 | 0.880 | 0.877 |
| 3 | 0.966 | — | 0.918 | 0.928 | 0.888 | 0.880 | 0.876 |
| 4 | 0.967 | 0.898 | 0.920 | 0.928 | 0.891 | 0.880 | 0.875 |
| 5 | 0.969 | 0.898 | 0.921 | 0.928 | 0.895 | 0.881 | 0.875 |
| $\Delta mAbs_{0-5}$ | −0.001 | −0.005 | −0.003 | −0.004 | 0.007 | −0.003 | −0.007 |

TABLE 3

Analysis of 6 e4/e4, and 11 e3/e3 samples by LEIT at different times by test 2

| | Absorbance (a.u., λ = 540 nm) Genotype/ID code | | | | | | |
|---|---|---|---|---|---|---|---|
| t (min) | 3/3 01-121 0.044 mg/mL | 3/3 01-122 0.044 mg/mL | 3/3 01-123 0.044 mg/mL | 3/3 01-124 0.044 mg/mL | 3/3 01-116 0.044 mg/mL | 3/3 01-117 0.044 mg/mL | 3/3 01-118 0.044 mg/mL |
| 0 | 1.026 | 0.978 | 0.944 | 0.898 | 0.990 | 0.992 | 0.967 |
| 1 | 1.020 | 0.976 | 0.927 | 0.893 | 0.988 | 0.986 | 0.964 |
| 2 | 1.018 | 0.976 | 0.926 | 0.890 | 0.986 | 0.984 | 0.962 |
| 3 | 1.018 | 0.976 | 0.925 | 0.889 | 0.986 | 0.983 | 0.962 |
| 4 | 1.018 | 0.978 | 0.925 | 0.889 | 0.986 | 0.984 | 0.962 |
| 5 | 1.018 | 0.980 | 0.926 | 0.889 | 0.987 | 0.984 | 0.963 |
| $\Delta mAbs_{0-5}$ | −0.008 | 0.002 | −0.018 | −0.009 | −0.003 | −0.008 | −0.004 |

| | Genotype/ID code | | | |
|---|---|---|---|---|
| t (min) | 3/3 01-120 0.044 mg/mL | 3/3 01-013 0.044 mg/mL | 3/3 01-008 0.044 mg/mL | 3/3 01-010 0.044 mg/mL |
| 0 | 0.993 | 0.973 | 1.046 | 1.086 |
| 1 | 0.976 | 0.969 | 1.040 | 1.074 |
| 2 | 0.975 | 0.968 | 1.038 | 1.070 |

TABLE 3-continued

| Analysis of 6 e4/e4, and 11 e3/e3 samples by LEIT at different times by test 2 | | | | |
|---|---|---|---|---|
| 3 | 0.973 | 0.968 | 1.039 | 1.069 |
| 4 | 0.973 | 0.969 | 1.042 | 1.071 |
| 5 | 0.974 | 0.971 | 1.046 | 1.073 |
| $\Delta mAbs_{0-5}$ | −0.019 | −0.002 | 0.000 | −0.013 |

| | Absorbance (a.u., λ = 540 nm) Genotype/ID code | | | | | |
|---|---|---|---|---|---|---|
| t (min) | 4/4 07-004 0.044 mg/mL | 4/4 07-005 0.044 mg/mL | 4/4 07-015 0.044 mg/mL | 4/4 02-001 0.044 mg/mL | 4/4 01-007 0.044 mg/mL | 4/4 05-009 0.044 mg/mL |
| 0 | 1.003 | 0.941 | 0.936 | 1.000 | 1.001 | 1.034 |
| 1 | 1.002 | 0.940 | 0.932 | 1.012 | 1.004 | 1.035 |
| 2 | 1.003 | 0.941 | 0.932 | 1.029 | 1.016 | 1.040 |
| 3 | 1.005 | 0.943 | 0.935 | 1.046 | 1.032 | 1.052 |
| 4 | 1.010 | 0.948 | 0.939 | 1.060 | 1.048 | 1.067 |
| 5 | 1.017 | 0.955 | 0.943 | 1.073 | 1.064 | 1.083 |
| $\Delta mAbs_{0-5}$ | 0.014 | 0.014 | 0.007 | 0.073 | 0.063 | 0.049 |

From the data derived from test 1, the authors of the invention concluded that the LEIT assay is able to distinguish between the different apoE plasma samples, except for one 3/4 plasma sample (see Table 2). Accordingly, optimal experimental conditions have been developed for an ApoE4 latex turbidimetric assay (see Table 4):

2.75 mg Anti-ApoE4/test 3.85 μl plasma sample

Total assay volume of 200 μl.

The invention claimed is:

1. An in vitro method for detection and/or quantification in a sample of an apolipoprotein selected from the group consisting of apoAI, apoAIV, apoCI, apoCII, apoCIII, apoE and apoJ (clusterin) or an isoform thereof, the method comprising:

(i) contacting the sample with a polystyrene surface under suitable conditions for a direct electrostatic and/or hydrophobic binding interaction between the apolipoprotein and the polystyrene surface, wherein the pH ranges from pH 2 to pH 10 during the contacting of the sample with the polystyrene surface;

(ii) contacting the surface to which the apolipoprotein or the isoform thereof is bound in step (i) with an antibody specific for said apolipoprotein or for said isoform thereof under suitable conditions for formation of a complex between the antibody and the apolipoprotein or the isoform thereof; and (iii) detecting the complex formed in step (ii), wherein the polystyrene surface is blocked with albumin prior to contacting the sample.

2. The method according to claim 1 wherein the apolipoprotein isoform is apoE4.

3. An in vitro method for determining in a sample a relative amount of a target isoform of a given apolipoprotein selected from the group consisting of apoAI, apoAIV, apoCI, apoCII, apoCIII, apoE and apoJ (clusterin) with respect to total content of said apolipoprotein in the sample, the method comprising:

(i) contacting the sample with a polystyrene surface under suitable conditions for forming a direct electrostatic and/or hydrophobic binding interaction between the apolipoprotein and the polystyrene surface;

(ii) contacting the surface to which the apolipoprotein is bound as formed in step (i) with a first antibody specific for said apolipoprotein target isoform and with a second antibody which is capable of binding to all isoforms of said apolipoprotein that are present in the sample, wherein said contacting with said first and second antibodies is carried out under conditions suitable for formation of a first complex comprising the first antibody and the apolipoprotein target isoform and for formation of a second complex comprising the second antibody and all the isoforms of said apolipoprotein that are present in the sample;

(iii) detecting a first level of the first complex formed in step (ii) and a second level of the second complex formed in step (ii); and (iv) determining relative amounts of said apolipoprotein target isoform with respect to the total apolipoprotein content based on the first and second levels detected in step (iii), wherein the polystyrene surface is blocked with albumin prior to contacting the sample.

4. The method of claim 3 wherein the polystyrene surface with which the sample is contacted in step (i) comprises a plurality of beads, particles, or wells in a plate, wherein the contacting with the first antibody and with the second antibody in step (ii) is performed in separate containers, each container containing part of the plurality of beads, particles or wells in the plate which comprise the surface, and wherein the detecting in step (iii) is carried out separately in each of said containers.

5. The method according to claim 3 wherein the apolipoprotein is apoE and said apolipoprotein target isoform is apoE4.

6. The method of claim 1, wherein the albumin is bovine serum albumin (BSA).

7. The method according to claim 1, wherein the polystyrene surface is treated with a washing solution after the binding step (i).

8. A method for determining the probability that a subject develops a neurodegenerative disease that comprises determining in a sample from said subject the levels of apoE4 isoform by a method according to claim 1, wherein if the apoE4 levels are above a reference value, then it is indicative that the subject has a high probability of suffering from a neurodegenerative disease.

9. The method according to claim 8, wherein the neurodegenerative disease is selected from the group consisting of Alzheimer's disease (AD), cerebral amyloid angiopathy (CAA), Down's syndrome-associated dementia, vascular dementia, Parkinson disease, dementia with Lewy bodies, and Creutzfeldt-Jakob disease.

10. The method of claim 1, wherein the polystyrene surface is:

(a) blocked with bovine serum albumin prior to the binding step (i); and/or (b) treated with a washing solution after the binding step (i).

11. The method of claim 3, wherein the albumin is bovine serum albumin (BSA).

12. The method of claim 3, wherein the polystyrene surface is treated with a washing solution after the binding step (i).

13. The method of claim 1, wherein the pH ranges from pH 4 to pH 10.

14. The method of claim 1, wherein the pH in steps (i) and (ii) is substantially the same.

15. The method of claim 1, wherein the pH ranges from pH 2 to pH 5 or from pH 8 to pH 10 during the contacting of the sample with the polystyrene surface.

16. The method of claim 1, wherein the sample is diluted in phosphate-buffered saline (PBS).

* * * * *